United States Patent
Sommadossi et al.

(10) Patent No.: US 11,690,860 B2
(45) Date of Patent: *Jul. 4, 2023

(54) TREATMENT OF HCV INFECTED PATIENTS WITH CIRRHOSIS

(71) Applicant: Atea Pharmaceuticals, Inc., Boston, MA (US)

(72) Inventors: Jean-Pierre Sommadossi, Boston, MA (US); Adel Moussa, Burlington, MA (US); Keith M. Pietropaolo, Boxford, MA (US); Xiao-Jian Zhou, Arlington, MA (US)

(73) Assignee: Atea Pharmaceuticals, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/065,149

(22) Filed: Oct. 7, 2020

(65) Prior Publication Data

US 2021/0015841 A1  Jan. 21, 2021

Related U.S. Application Data

(63) Continuation of application No. PCT/US2019/026837, filed on Apr. 10, 2019.

(60) Provisional application No. 62/679,573, filed on Jun. 1, 2018, provisional application No. 62/655,697, filed on Apr. 10, 2018.

(51) Int. Cl.
A61K 31/7076 (2006.01)
A61P 31/14 (2006.01)

(52) U.S. Cl.
CPC .......... A61K 31/7076 (2013.01); A61P 31/14 (2018.01)

(58) Field of Classification Search
None
See application file for complete search history.

(56) References Cited

U.S. PATENT DOCUMENTS

| | | |
|---|---|---|
| 5,977,061 A | 11/1999 | Holy et al. |
| 6,348,587 B1 | 2/2002 | Schinazi et al. |
| 6,602,999 B1 | 8/2003 | Kumar et al. |
| 6,660,721 B2 | 12/2003 | Devos et al. |
| 6,777,395 B2 | 8/2004 | Bhat et al. |
| 6,784,166 B2 | 8/2004 | Devos et al. |
| 6,812,219 B2 | 11/2004 | LaColla et al. |
| 6,908,924 B2 | 6/2005 | Watanabe et al. |
| 6,911,424 B2 | 6/2005 | Schinazi et al. |
| 6,914,054 B2 | 7/2005 | Sommadossi et al. |
| 6,949,522 B2 | 9/2005 | Otto et al. |
| 7,094,770 B2 | 8/2006 | Watanabe et al. |
| 7,105,493 B2 | 9/2006 | Sommadossi et al. |
| 7,105,499 B2 | 9/2006 | Carroll et al. |
| 7,125,855 B2 | 10/2006 | Bhat et al. |
| 7,138,376 B2 | 11/2006 | Gosselin et al. |
| 7,148,206 B2 | 12/2006 | Sommadossi et al. |
| 7,157,441 B2 | 1/2007 | Sommadossi et al. |
| 7,163,929 B2 | 1/2007 | Sommadossi et al. |
| 7,169,766 B2 | 1/2007 | Sommadossi et al. |
| 7,192,936 B2 | 3/2007 | LaColla et al. |
| 7,202,224 B2 | 4/2007 | Eldrup et al. |
| 7,211,570 B2 | 5/2007 | Schinazi et al. |
| 7,268,119 B2 | 9/2007 | Cook et al. |
| 7,285,658 B2 | 10/2007 | Cook et al. |
| 7,307,065 B2 | 12/2007 | Schinazi et al. |
| 7,323,449 B2 | 1/2008 | Olsen et al. |
| 7,339,054 B2 | 3/2008 | Xu et al. |
| 7,365,057 B2 | 4/2008 | LaColla et al. |
| 7,384,924 B2 | 6/2008 | LaColla et al. |
| 7,388,002 B2 | 6/2008 | Babu et al. |
| 7,429,571 B2 | 9/2008 | Chand et al. |
| 7,429,572 B2 | 9/2008 | Clark |
| 7,456,155 B2 | 11/2008 | Sommadossi et al. |
| 7,495,006 B2 | 2/2009 | Liotta et al. |
| 7,514,410 B2 | 4/2009 | Babu et al. |
| 7,534,767 B2 | 5/2009 | Butora et al. |
| 7,547,704 B2 | 6/2009 | LaColla et al. |
| 7,560,434 B2 | 7/2009 | Babu et al. |

(Continued)

FOREIGN PATENT DOCUMENTS

| | | |
|---|---|---|
| CN | 103435672 A | 12/2013 |
| CN | 103980332 A | 8/2014 |

(Continued)

OTHER PUBLICATIONS

Noriaki Hirayama, Handbook for Producing Organic Compound Crystals, 2008, pp. 17-23, 37-40, 45-51, and 57-65 (reference showing a well-known technique) and English partial translation.
Nguyen, Lien et al., International Journal of Biomedical Science: Chiral Drugs: An Overview; Jun. 2, 2006(20; 85-100).
U.S. Appl. No. 17/009,595, Sommadossi et al., filed Sep. 1, 2020.
U.S. Appl. No. 17/094,541, Sommadossi et al., filed Nov. 10, 2020.
U.S. Appl. No. 17/184,445, Sommadossi et al., filed Feb. 24, 2021.

(Continued)

*Primary Examiner* — Patrick T Lewis
(74) *Attorney, Agent, or Firm* — Knowles Intellectual Property Strategies, LLC

(57) ABSTRACT

A pharmaceutical composition that includes a compound of the structure:

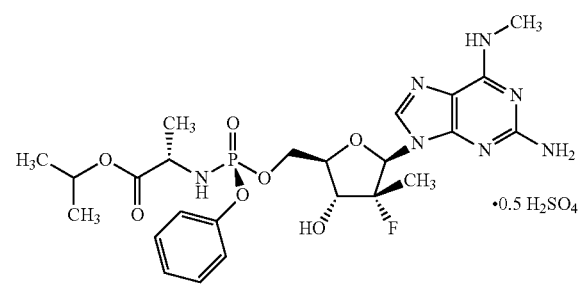

to treat an HCV infected patient with cirrhosis, and uses thereof.

37 Claims, 15 Drawing Sheets

(56) References Cited

U.S. PATENT DOCUMENTS

| | | |
|---|---|---|
| 7,560,550 B2 | 7/2009 | Doring et al. |
| 7,582,618 B2 | 9/2009 | Sommadossi et al. |
| 7,601,820 B2 | 10/2009 | Wang et al. |
| 7,608,597 B2 | 10/2009 | Sommadossi et al. |
| 7,608,599 B2 | 10/2009 | Klumpp et al. |
| 7,608,600 B2 | 10/2009 | Storer et al. |
| 7,608,601 B2 | 10/2009 | Devos et al. |
| 7,625,875 B2 | 12/2009 | Gosselin et al. |
| 7,632,821 B2 | 12/2009 | Butora et al. |
| 7,635,689 B2 | 12/2009 | LaColla et al. |
| 7,638,502 B2 | 12/2009 | Schinazi et al. |
| 7,652,001 B2 | 1/2010 | Hostetler et al. |
| 7,662,798 B2 | 2/2010 | LaColla et al. |
| 7,662,938 B2 | 2/2010 | Schinazi et al. |
| 7,691,603 B2 | 4/2010 | DeFrees |
| 7,713,941 B2 | 5/2010 | Cook et al. |
| 7,718,790 B2 | 5/2010 | Stuyver et al. |
| 7,749,983 B2 | 7/2010 | Hostetler et al. |
| 7,772,208 B2 | 8/2010 | Schinazi et al. |
| 7,824,851 B2 | 11/2010 | Sommadossi et al. |
| 7,842,672 B2 | 11/2010 | Boojamra et al. |
| RE42,015 E | 12/2010 | Watanabe et al. |
| 7,879,815 B2 | 2/2011 | MacCoss et al. |
| 7,902,202 B2 | 3/2011 | Sommadossi et al. |
| 7,919,247 B2 | 4/2011 | Stuyver et al. |
| 7,932,240 B2 | 4/2011 | Dousson et al. |
| 7,951,789 B2 | 5/2011 | Sommadossi et al. |
| 7,964,580 B2 | 6/2011 | Sofia et al. |
| 7,973,013 B2 | 7/2011 | Cho et al. |
| 7,994,139 B2 | 8/2011 | Babu et al. |
| 8,008,264 B2 | 8/2011 | Butler et al. |
| 8,012,941 B2 | 9/2011 | Cho et al. |
| 8,012,942 B2 | 9/2011 | Butler et al. |
| 8,071,567 B2 | 12/2011 | Devos et al. |
| 8,071,568 B2 | 12/2011 | Narjes et al. |
| 8,093,380 B2 | 1/2012 | Wang et al. |
| 8,114,994 B2 | 2/2012 | Liotta et al. |
| 8,114,997 B2 | 2/2012 | Otto et al. |
| 8,119,607 B2 | 2/2012 | Francom et al. |
| 8,133,870 B2 | 3/2012 | Babu et al. |
| 8,148,349 B2 | 4/2012 | Meppen et al. |
| 8,163,703 B2 | 4/2012 | Babu et al. |
| 8,168,583 B2 | 5/2012 | Schinazi et al. |
| 8,173,621 B2 | 5/2012 | Du et al. |
| 8,193,372 B2 | 6/2012 | Dousson et al. |
| 8,242,085 B2 | 8/2012 | Babu et al. |
| 8,299,038 B2 | 10/2012 | Sommadossi et al. |
| 8,318,682 B2 | 11/2012 | Butler et al. |
| 8,324,179 B2 | 12/2012 | Chen et al. |
| 8,334,270 B2 | 12/2012 | Sofia et al. |
| 8,343,937 B2 | 1/2013 | Sommadossi et al. |
| 8,362,068 B2 | 1/2013 | Dousson et al. |
| 8,399,428 B2 | 3/2013 | Wagner |
| 8,399,429 B2 | 3/2013 | Jonckers et al. |
| 8,415,308 B2 | 4/2013 | Cho et al. |
| 8,415,309 B2 | 4/2013 | Francom et al. |
| 8,415,321 B2 | 4/2013 | Schinazi et al. |
| 8,415,322 B2 | 4/2013 | Clark |
| 8,431,588 B2 | 4/2013 | Jonckers et al. |
| 8,440,813 B2 | 5/2013 | Babu et al. |
| 8,455,451 B2 | 6/2013 | Cho et al. |
| 8,470,834 B2 | 6/2013 | Kwong et al. |
| 8,481,510 B2 | 7/2013 | Jonckers et al. |
| 8,481,712 B2 | 7/2013 | Bhat et al. |
| 8,481,713 B2 | 7/2013 | Wang et al. |
| 8,492,539 B2 | 7/2013 | Chun et al. |
| 8,501,699 B2 | 8/2013 | Francom et al. |
| 8,507,460 B2 | 8/2013 | Surleraux et al. |
| 8,541,434 B2 | 9/2013 | Kwong et al. |
| 8,551,973 B2 | 10/2013 | Bao et al. |
| 8,552,021 B2 | 10/2013 | Jonckers et al. |
| 8,563,530 B2 | 10/2013 | Chang et al. |
| 8,575,119 B2 | 11/2013 | Wang et al. |
| 8,580,765 B2 | 11/2013 | Sofia et al. |
| 8,609,627 B2 | 12/2013 | Cho et al. |
| 8,618,076 B2 | 12/2013 | Ross et al. |
| 8,629,263 B2 | 1/2014 | Ross et al. |
| 8,633,309 B2 | 1/2014 | Ross et al. |
| 8,637,475 B1 | 1/2014 | Storer et al. |
| 8,642,756 B2 | 2/2014 | Ross et al. |
| 8,658,616 B2 | 2/2014 | McGuigan et al. |
| 8,673,926 B2 | 3/2014 | Chu |
| 8,674,085 B2 | 3/2014 | Sommadossi et al. |
| 8,680,071 B2 | 3/2014 | Surleraux et al. |
| 8,691,788 B2 | 4/2014 | Sommadossi et al. |
| 8,697,694 B2 | 4/2014 | Arasappan et al. |
| 8,715,638 B2 | 5/2014 | Kwong et al. |
| 8,716,262 B2 | 5/2014 | Sofia et al. |
| 8,716,263 B2 | 5/2014 | Chun et al. |
| 8,735,345 B2 | 5/2014 | Porter et al. |
| 8,735,372 B2 | 5/2014 | Du et al. |
| 8,735,569 B2 | 5/2014 | Ross et al. |
| 8,742,101 B2 | 6/2014 | Storer et al. |
| 8,759,318 B2 | 6/2014 | Chamberlain et al. |
| 8,759,372 B2 | 6/2014 | Roberts et al. |
| 8,759,510 B2 | 6/2014 | Du et al. |
| 8,765,710 B2 | 7/2014 | Sofia et al. |
| 8,772,474 B2 | 7/2014 | Beigelman et al. |
| 8,802,840 B2 | 8/2014 | Francom et al. |
| 8,815,829 B2 | 8/2014 | Schinazi et al. |
| 8,816,074 B2 | 8/2014 | Chu et al. |
| 8,841,275 B2 | 9/2014 | Du et al. |
| 8,846,638 B2 | 9/2014 | Or et al. |
| 8,846,896 B2 | 9/2014 | Serebryany et al. |
| 8,853,171 B2 | 10/2014 | Butler et al. |
| 8,859,595 B2 | 10/2014 | Coats et al. |
| 8,859,756 B2 | 10/2014 | Ross et al. |
| 8,871,737 B2 | 10/2014 | Smith et al. |
| 8,871,785 B2 | 10/2014 | Boojamra et al. |
| 8,877,731 B2 | 11/2014 | Beigelman et al. |
| 8,877,733 B2 | 11/2014 | Cho et al. |
| 8,889,159 B2 | 11/2014 | Cleary et al. |
| 8,889,701 B1 | 11/2014 | Ivachtchenko et al. |
| 8,895,531 B2 | 11/2014 | Shi |
| 8,895,723 B2 | 11/2014 | Serebryany et al. |
| 8,906,880 B2 | 12/2014 | Du et al. |
| 8,912,321 B2 | 12/2014 | Axt et al. |
| 8,921,384 B2 | 12/2014 | Chu |
| 8,927,513 B2 | 1/2015 | Manoharan et al. |
| 8,933,052 B2 | 1/2015 | Jonckers et al. |
| 8,946,244 B2 | 2/2015 | Chu et al. |
| 8,951,985 B2 | 2/2015 | Surleraux et al. |
| 8,957,045 B2 | 2/2015 | Sofia et al. |
| 8,957,046 B2 | 2/2015 | Du et al. |
| 8,980,865 B2 | 3/2015 | Wang et al. |
| 9,012,427 B2 | 4/2015 | Blatt et al. |
| 9,012,428 B2 | 4/2015 | Jonckers et al. |
| 9,045,520 B2 | 6/2015 | Chun et al. |
| 9,061,041 B2 | 6/2015 | Girijavallabhan et al. |
| 9,085,573 B2 | 7/2015 | Du et al. |
| 9,085,599 B2 | 7/2015 | Or et al. |
| 9,090,642 B2 | 7/2015 | Cho et al. |
| 9,109,001 B2 | 8/2015 | Parsy et al. |
| 9,139,604 B2 | 9/2015 | Boojamra et al. |
| 9,156,872 B2 | 10/2015 | Girijavallabhan et al. |
| 9,173,893 B2 | 11/2015 | Cho et al. |
| 9,187,515 B2 | 11/2015 | Mayes et al. |
| 9,192,621 B2 | 11/2015 | Mayes et al. |
| 9,211,300 B2 | 12/2015 | Mayes et al. |
| 9,243,025 B2 | 1/2016 | Surleraux et al. |
| 9,249,174 B2 | 2/2016 | Beigelman et al. |
| 9,339,541 B2 | 5/2016 | Dousson et al. |
| 9,351,989 B2 | 5/2016 | McGuigan et al. |
| 9,403,863 B2 | 8/2016 | Surleraux et al. |
| 9,408,863 B2 | 8/2016 | Verma et al. |
| 9,447,132 B2 | 9/2016 | Deshpande et al. |
| 9,598,457 B2 | 3/2017 | Smith et al. |
| 9,603,863 B2 | 3/2017 | Blatt et al. |
| 9,603,864 B2 | 3/2017 | Blatt et al. |
| 9,758,544 B2 | 9/2017 | Beigelman et al. |
| 9,815,864 B2 | 11/2017 | Beigelman et al. |
| 9,822,137 B2 | 11/2017 | Dehaen et al. |
| 9,828,410 B2 | 11/2017 | Sommadossi et al. |
| 9,890,188 B2 | 2/2018 | Wang et al. |

(56) References Cited

U.S. PATENT DOCUMENTS

| | | |
|---|---|---|
| 10,000,523 B2 | 6/2018 | Sommadossi et al. |
| 10,005,810 B2 | 6/2018 | McGuigan et al. |
| 10,005,811 B2 | 6/2018 | Sommadossi et al. |
| 10,239,911 B2 | 3/2019 | Sommadossi et al. |
| 10,519,186 B2 | 12/2019 | Moussa et al. |
| 10,874,687 B1 | 12/2020 | Sommadossi et al. |
| 2002/0045599 A1 | 4/2002 | Arimilli et al. |
| 2002/0058635 A1 | 5/2002 | Averett |
| 2003/0087873 A1 | 5/2003 | Stuyver et al. |
| 2004/0063658 A1 | 4/2004 | Roberts et al. |
| 2004/0229839 A1 | 11/2004 | Babu et al. |
| 2004/0259934 A1 | 12/2004 | Olsen et al. |
| 2005/0038240 A1 | 2/2005 | Connolly et al. |
| 2005/0203044 A1 | 9/2005 | Zinnen |
| 2007/0265222 A1 | 11/2007 | MacCoss et al. |
| 2008/0207554 A1 | 8/2008 | Beigelman et al. |
| 2009/0156545 A1 | 6/2009 | Hostetler et al. |
| 2009/0176732 A1 | 7/2009 | Beigelman et al. |
| 2009/0181921 A1 | 7/2009 | Blatt et al. |
| 2009/0318380 A1 | 12/2009 | Sofia et al. |
| 2010/0137576 A1 | 6/2010 | Stec et al. |
| 2010/0240604 A1 | 9/2010 | Beigelman et al. |
| 2010/0249068 A1 | 9/2010 | Beigelman et al. |
| 2010/0279969 A1 | 11/2010 | Schinazi et al. |
| 2010/0331397 A1 | 12/2010 | Beigelman et al. |
| 2011/0091943 A1 | 4/2011 | Gallou et al. |
| 2011/0257121 A1 | 10/2011 | Chang et al. |
| 2012/0070411 A1 | 3/2012 | Beigelman et al. |
| 2012/0135951 A1 | 5/2012 | Schinazi et al. |
| 2013/0064794 A1 | 3/2013 | Surleraux et al. |
| 2013/0225636 A1 | 8/2013 | Roberts et al. |
| 2013/0244966 A1 | 9/2013 | Milne et al. |
| 2013/0315868 A1 | 11/2013 | Mayes et al. |
| 2014/0038916 A1 | 2/2014 | Wang et al. |
| 2014/0066395 A1 | 3/2014 | Cho et al. |
| 2014/0112886 A1 | 4/2014 | Moussa et al. |
| 2014/0212382 A1 | 7/2014 | Schinazi et al. |
| 2014/0235566 A1 | 8/2014 | Amblard et al. |
| 2015/0011481 A1 | 1/2015 | Vilchez et al. |
| 2015/0011497 A1 | 1/2015 | Beigelman et al. |
| 2015/0057243 A1 | 2/2015 | Zhou et al. |
| 2015/0105341 A1 | 4/2015 | Beigelman et al. |
| 2015/0150897 A1 | 6/2015 | Denning et al. |
| 2015/0183818 A1 | 7/2015 | Tran et al. |
| 2016/0002281 A1 | 1/2016 | Mayes et al. |
| 2016/0220595 A1 | 8/2016 | Liotta et al. |
| 2016/0257706 A1 | 9/2016 | Sommadossi et al. |
| 2016/0271162 A1 | 9/2016 | Moussa et al. |
| 2017/0022242 A1 | 1/2017 | Herdewyn et al. |
| 2017/0029456 A1 | 2/2017 | Dousson et al. |
| 2017/0275322 A1 | 9/2017 | Oinho et al. |
| 2018/0009836 A1 | 1/2018 | Sommadossi et al. |
| 2019/0153017 A1 | 5/2019 | Sommadossi et al. |
| 2019/0201433 A1 | 7/2019 | Sommadossi et al. |
| 2020/0087339 A1 | 3/2020 | Moussa et al. |
| 2021/0009628 A1 | 1/2021 | Sommadossi et al. |
| 2021/0277045 A1 | 9/2021 | Moussa et al. |

FOREIGN PATENT DOCUMENTS

| | | |
|---|---|---|
| CN | 105646629 A | 6/2016 |
| CN | 106188192 A | 12/2016 |
| EP | 547008 A1 | 6/1993 |
| EP | 398231 B1 | 7/1997 |
| WO | WO 1998/16184 | 4/1998 |
| WO | WO 2001/009143 A1 | 2/2001 |
| WO | WO 2001/90121 A2 | 11/2001 |
| WO | WO 2001/92282 A2 | 12/2001 |
| WO | WO 2002/32920 A2 | 4/2002 |
| WO | WO 2003/033508 A1 | 4/2003 |
| WO | WO 2003/039523 A2 | 5/2003 |
| WO | WO 2003/062256 A1 | 7/2003 |
| WO | WO 2003/093290 A2 | 11/2003 |
| WO | WO 2004/002999 A2 | 1/2004 |
| WO | WO 2004/003000 A2 | 1/2004 |
| WO | WO 2004/014312 A2 | 2/2004 |
| WO | WO 2004/052906 A2 | 6/2004 |
| WO | WO 2004/074350 A2 | 9/2004 |
| WO | WO 2004/091499 A2 | 10/2004 |
| WO | WO 2004/106356 A1 | 12/2004 |
| WO | WO 2005/000864 A1 | 1/2005 |
| WO | WO 2005/020884 A2 | 3/2005 |
| WO | WO 2005/021568 A2 | 3/2005 |
| WO | WO 2005/084192 A2 | 9/2005 |
| WO | WO 2005/090370 A1 | 9/2005 |
| WO | WO 2006/012078 A2 | 2/2006 |
| WO | WO 2006/063149 A1 | 6/2006 |
| WO | WO 2006/063717 A2 | 7/2006 |
| WO | WO 2006/094347 A1 | 9/2006 |
| WO | WO 2006/102533 A2 | 9/2006 |
| WO | WO 2006/121820 A1 | 11/2006 |
| WO | WO 2006/130217 A2 | 12/2006 |
| WO | WO 2007/022073 A2 | 2/2007 |
| WO | WO 2007/112028 A2 | 10/2007 |
| WO | WO 2007/130783 A1 | 11/2007 |
| WO | WO 2008/012555 A2 | 1/2008 |
| WO | WO 2008/048128 A1 | 4/2008 |
| WO | WO 2008/062206 A2 | 5/2008 |
| WO | WO 2008/095040 A2 | 10/2008 |
| WO | WO 2009/001097 A2 | 12/2008 |
| WO | WO 2009/003042 A1 | 12/2008 |
| WO | WO 2009/067409 A1 | 5/2009 |
| WO | WO 2009/086192 A1 | 7/2009 |
| WO | WO 2009/086201 A1 | 7/2009 |
| WO | WO 2009/129120 A2 | 10/2009 |
| WO | WO 2010/081082 A2 | 7/2010 |
| WO | WO 2010/091386 A2 | 8/2010 |
| WO | WO 2010/108135 A1 | 9/2010 |
| WO | WO 2010/145778 | 12/2010 |
| WO | WO 2011/005595 A1 | 1/2011 |
| WO | WO 2011/005860 A2 | 1/2011 |
| WO | WO 2012/041965 A1 | 4/2012 |
| WO | WO 2012/048013 A2 | 4/2012 |
| WO | WO 2012/092484 A2 | 7/2012 |
| WO | WO 2012/125900 A1 | 9/2012 |
| WO | WO 2012/154321 A1 | 11/2012 |
| WO | WO 2012/158811 A2 | 11/2012 |
| WO | WO 2013/009737 A1 | 1/2013 |
| WO | WO 2013/019874 A1 | 2/2013 |
| WO | WO 2013/039855 A1 | 3/2013 |
| WO | WO 2013/039920 A1 | 3/2013 |
| WO | WO 2013/044030 A1 | 3/2013 |
| WO | WO 2013/059735 A1 | 4/2013 |
| WO | WO 2013/090420 A2 | 6/2013 |
| WO | WO 2013/096680 A1 | 6/2013 |
| WO | WO 2013/142125 A1 | 9/2013 |
| WO | WO 2013/142157 A1 | 9/2013 |
| WO | WO 2013/142159 A1 | 9/2013 |
| WO | WO 2013/151975 A1 | 10/2013 |
| WO | WO 2013/177219 A1 | 11/2013 |
| WO | WO 2013/187978 A1 | 12/2013 |
| WO | WO 2014/008236 A1 | 1/2014 |
| WO | WO 2014/047117 A1 | 3/2014 |
| WO | WO 2014/052638 A1 | 4/2014 |
| WO | WO 2014/063019 A1 | 4/2014 |
| WO | WO 2014/076490 A1 | 5/2014 |
| WO | WO 2014/082935 A1 | 6/2014 |
| WO | WO 2014/100498 A1 | 6/2014 |
| WO | WO 2014/100505 A1 | 6/2014 |
| WO | WO 2014/12443 0 A1 | 8/2014 |
| WO | WO 2014/120981 A1 | 8/2014 |
| WO | WO 2014/13793 0 A1 | 9/2014 |
| WO | WO 2014/169278 A1 | 10/2014 |
| WO | WO 2014/169280 A2 | 10/2014 |
| WO | WO 2014/209979 A1 | 12/2014 |
| WO | WO 2015/038596 A1 | 3/2015 |
| WO | WO 2015/053662 A1 | 4/2015 |
| WO | WO 2015/081133 A2 | 6/2015 |
| WO | WO 2015/095305 A1 | 6/2015 |
| WO | WO 2015/158913 A1 | 10/2015 |
| WO | WO 2016/041877 A1 | 3/2016 |
| WO | WO 2016/100441 A1 | 6/2016 |
| WO | WO 2016/100569 A1 | 6/2016 |
| WO | WO 2016/144918 A1 | 9/2016 |

(56) References Cited

FOREIGN PATENT DOCUMENTS

| WO | WO 2016/145142 A1 | 9/2016 |
|----|-------------------|--------|
| WO | WO 2018/013937 A1 | 1/2018 |
| WO | WO 2018/048937 A1 | 3/2018 |
| WO | WO 2019/200005 A1 | 10/2019 |

OTHER PUBLICATIONS

US, 2021/0087217, A1, U.S. Appl. No. 17/118,314, Moussa, et al., Mar. 25, 2021.
U.S. Appl. No. 17/306,643, Sommadossi, filed May 3, 2021.
U.S. Appl. No. 17/306,659, Mousa, filed May 3, 2021.
U.S. Appl. No. 17/306,674, Sommadossi, filed May 3, 2021.
Berliba, et al., "Safety, Pharmacokinetics, and Antiviral Activity of AT-527, a Novel Purine Nucleotide Prodrug, in Hepatitis C Virus-Infected Subjects with or without Cirrhosis," Antimicrobial Agents and Chemotherapy, Dec. 2019, vol. 63, Issue 12.
Good, et al., "Preclinical evaluation of AT-527, a novel guanosine nucleotide prodrug with potent, pan-genotypic activity against hepatitis C virus," Plos One, https://doi.org/10.1371/journal.pone.0227104, Jan. 8, 2020.
U.S. Pat. No. 9,828,410, B2, U.S. Appl. No. 15/063,461, Sommadossi et al., Nov. 28, 2017.
U.S. Pat. No. 10,000,523, B2, U.S. Appl. No. 15/782,628, Sommadossi et al., Jun. 19, 2018.
U.S. Pat. No. 10,005,811, B2, U.S. Appl. No. 15/782,638, Sommadossi et al., Jun. 26, 2018.
U.S. Pat. No. 10,202,412, B2, U.S. Appl. No. 15/645,701, Sommadossi et al., Feb. 12, 2019.
U.S. Pat. No. 10,239,911, B2, U.S. Appl. No. 16/001,549, Sommadossi et al., Mar. 26, 2019.
U.S. Pat. No. 10,519,186, B2, U.S. Appl. No. 15/885,630, Mousa et al., Dec. 31, 2019.
U.S. Pat. No. 10,815,266, B2, U.S. Appl. No. 16/278,621, Sommadossi et al., Oct. 24, 2020.
US, 2019/0201433, A1, U.S. Appl. No. 16/293,423, Sommadossi et al., Jul. 4, 2019.
US 2020/0087339, A1, U.S. Appl. No. 16/687,136, Moussa et al., Mar. 19, 2020.
US, 2020/0179415, A1, U.S. Appl. No. 16/703,599, Sommadossi et al., Jun. 11, 2020.
US, 2020-0222442, A1, U.S. Appl. No. 16/821,850, Sommadossi et al., Jul. 16, 2020.
US, 2020/0308215, A1, U.S. Appl. No. 16/900,397, Sommadossi et al., Oct. 1, 2020.
US, 2020/0331955, A1 U.S. Appl. No. 16/918,898, Sommadossi et al., Oct. 22, 2020.
US, 2020/0331956, A1, U.S. Appl. No. 16/918,914, Sommadossi et al., Oct. 22, 2020.
US, 2020/0331954, A1, U.S. Appl. No. 16/918,918, Mousa et al., Oct. 22, 2020.
U.S. Appl. No. 17/017,443, filed Sep. 10, 2020, Sommadossi et al.
U.S. Appl. No. 17/028,724, filed Sep. 22, 2020, Sommadossi et al.
Ahmad, T. et al. "Cardiac dysfunction associated with a nucleotide polymerase inhibitor for treatment of hepatitis C", Hepatology 2015, 62, 409.
Ahn et al., "Biochemical characterization of a recombinant SARS coronavirus nsp12 RNA-dependent RNA polymerase capable of copying viral RNA templates", Arch Virol. 2012, 157, 2095-2104.
Atea Corporate Presentation, "Rapidly advancing transformative therapies for patients with life-threatening viral diseases", May 1, 2020.
Berge, M.S. et al. "Pharmaceutical Salts", Journal of Pharmaceutical Sciences, 1977, 66, 1.
Chang, W. et al. "Discovery of PSI-353661, a Novel Purine Nucleotide Prodrug for the Treatment of HCV Infection", ACS Med Chem Lett. 2011, 2, 130.
Cretton-Scott, E. et al. "In vitro antiviral activity and pharmacology of idx184, a novel and potent inhibitor of hcv replication", (Abstract 588) J. Hepatol. 2008, 48, Supplement 2, S220.
Freeman et al., "2-amino-9(3-azido-2,3-dideoxy-β-D-erythro-pentofuranosyl)-6-Substituted-9H-Purines: Synthesis and Anti-HIV Activity", Bioorganic and Medicinal Chemistry, 1995; 3(4): 447-448.
Gao et al., "Structure of the RNA-dependent RNA polymerase from COVID-19 virus", Science, 2020, 368(6492), 779-782.
Good, S. et al., "AT-337, AT-511, and its Salt Form, AT-527: Novel Potent and Selective Pan-genotypic Purine Nucleotide Prodrug Inhibitors of HCV Polymerase" presented at the AASLD 2017 Liver Meeting; Oct. 20, 2017-Oct. 24, 2017; Washington, D.C.
Herman, B. et al., "Substrate mimicry: HIV-1 reverse transcriptase recognizes 6-modified-30-azido-20,30-dideoxyguanosine-50-triphosphates as adenosine analogs" Nucleic Acids Research 2012, 40, 381.
Hoffman, M. et al., "SARS-CoV-2 Cell Entry Depends on ACE2 and TMPRSS2 and Is Blocked by a Clinically Proven Protease Inhibitor", Cell, 2020, 181(2), 271-280.
Huang et al., "Impact of solid-state properties on developability assessment of drug candidates" Advanced Drug Delivery Reviews. 2004, 56, 321.
Huang et al., "Clinical features of patients infected with 2019 novel coronavirus in Wuhan, China", Lancet, 2020, 395(10223), 497-506.
Lau et al., "Severe acute respiratory syndrome coronavirus-like virus in Chinese horseshoe bats", PNAS, 2005, 102(39), 14040-14045.
Luan et al., "Spike protein recognition of mammalian ACE2 predicts the host range and an optimized ACE2 for SARS-CoV-2 infection", Biochem. Biophys. Res. Commun., 2020, 526(1), 165-169.
McGuigan, C. et al., "Design, synthesis and evaluation of a novel double pro-drug: INX-08189. A new clinical candidate for hepatitis C virus" Bioorganic & Medicinal Chemistry Letters 2010, 20, 4850.
McGuigan, C. et al., "Dual pro-drugs of 2'-C-methyl guanosine monophosphate as potent and selective inhibitors of hepatitis C virus" Bioorganic & Medicinal Chemistry Letters 2011, 21, 6007.
Murakami, E. et al., "Adenosine Deaminase-like Protein 1 (ADAL1): Characterization and Substrate Specificity in the Hydrolysis of N6- or O6-Substituted Purine or 2-Aminopurine Nucleoside Monophosphates" J Med Chem 2011, 54, 5902.
Poordad et al., "Daclatasvir with Sofosbuvir and Ribavirin for Hepatitis C Virus Infection with Advanced Cirrhosis or Post-Liver Transplantation Recurrence", Hepatology, 2016, 63, 1493.
Pradere, U. et al., "Synthesis of 5'-Methylene-Phosphonate Furanonucleoside Prodrugs: Application to D-2'-Deoxy-2'-α-fluoro-2'-β-C-methyl Nucleosides", Organic Letters 2012, 14, 4426.
Reddy, P. et al., "2'-Deoxy-2'-α-fluoro-2'-β-C-methyl 3', 5'-cyclic phosphate nucleotide prodrug analogs as inhibitors of HCV NS5B polymerase: Discovery of PSI-352938", Bioorganic & Medicinal Chemistry Letters 2010, 20, 7376.
Rest et al., "SARS associated coronavirus coronaviruses has a recombinant polymerase and coronaviruses have a history of host-shifting", Infect Genet Evol , 2003, 3(3), 219-225.
Schoeman and Fielding, "Coronavirus envelope protein: current knowledge", Virology 2019, 16(69), 1-22.
Serajuddin, A.T.M., "Salt formation to improve drug solublity", Advanced Drug Delivery Reviews, 2007, 59, 603.
Sofia, M.J. "Nucleotide Prodrugs for HCV Therapy," Antiviral Chemistry & Chemotherapy, 2011; 22, 23.
Stahl et al., "Handbook of Pharmaceutical Salts Properties, Selection, and Use", International Union of Pure and Applied Chemistry (IUPAC), 2002 (Chapters 6 and 7).
Subissi et al., "One severe acute respirator syndrome coronavirus protien complex integrates processive RNA polymerase and exonuclease activities", Proc. Natl. Acad. Sci., 2014, 111(37), E3900-E3909.
Tao, S., et al., "Comparison of Three 2'-C-Methyl Guanosine Prodrugs for Hepatitis C including a Novel $^2$-D-2'-C-Me-2,6-Diaminopurine Ribonucleoside Phosphoramidate (RS-1389): Interspecies Hepatocyte and Human Cardiomyocyte Metabolism Profiles", The Liver Meeting 2014. Boston, MA, USA. Nov. 6-11, 2014.

(56) References Cited

OTHER PUBLICATIONS

Yang et al., "Targeting the Endocytic Pathway and Autophagy Process as a Novel Therapeutic Strategy in COVID-19", Int. J. Biol. Sci. 2020, 16(10), 1724-1731.
Zhang et al., "Synthesis and evaluation of 30-azido-20,30-dideoxypurine nucleosides as inhibitors of human immunodeficiency virus", Bioorganic and Medicinal Chemistry Letters 2010, 20, 60.
Zhou, L. et al., "β-D-'-C-Methyl-2,6-diaminopurine Ribonucleoside Phosphoramidates are Potent and Selective Inhibitors of Hepatitis C Virus (HCV) and Are Bioconverted Intracellularly to Bioactive 2,6-Diaminopurine and Guanosine 5'-Triphosphate Forms" J Med Chem 2015, 58, 3445.
Zhou, X. et al., "A Phase 1a Study of AT-527, a Novel Pan-Genotypic Purine Nucleotide Prodrug Inhibitor of Hepatitis C Virus (HCV)", presented at The Liver Meeting 2017; Oct. 23, 2017; Washington, D.C.
Zhou, X. et al., "AT-527, a pan-genotypic purine nucleotide prodrug, exhibits potent antiviral activity in subjects with chronic hepatitis C", presented at The International Liver Congress 2018; Apr. 13, 2018; Paris, France.
Zhou et al., "A pneumonia outbreak associated with a new coronavirus of probable bat origin", Nature, 2020, 579, 270.
M. Grif and K, 2012, pp. 525-549.
Papageorgiou, Louis et al. Mol. BioSyst., Jan. 28, 2016, 12(7), 2080-2093.
U.S. Appl. No. 17/482,224, Sommadossi, filed Sep. 22, 2021.
Afzal et al., Diagnostically untypable hepatitis C virus variants: It is time to resolve the problem. World Journal of Gastroenterology, Dec. 2014, vol. 20(46), pp. 17690-17692.
Forns et al., Glecaprevir plus pibrentasvir for chronic hepatitis C virus genotype I, 2, 4, 5, or 6 infection in adults with compensated cirrhosis (EXPEDITION-1): a single-arm, open-label, multicentre phase 3 trial. The Lancet Infectious Diseases, 2017, vol. 17, pp. 1062-1068, doi: 10.1016/81473-3099(17)30496-6).
Kanda, T., Interferon-free treatment for HCV-infected patients with decompensated cirrhosis, Hepatology International, 2016, vol. 11, No. 1, pp. 38-44.

TREATMENT OF HCV INFECTED PATIENTS WITH CIRRHOSIS

CROSS-REFERENCE TO RELATED APPLICATIONS

This application is a continuation of International Application No. PCT/US2019/026837 filed in the International Patent Cooperation Treaty, U.S. Receiving Office on Apr. 10, 2019, which claims the benefit and priority to provisional U.S. Provisional Applications No. 62/655,697, filed on Apr. 10, 2018; and Application No. 62/679,573, filed on Jun. 1, 2018. These applications are incorporated by reference in their entirety for all purposes.

FIELD OF THE INVENTION

The present invention is the use of the hemi-sulfate salt of a selected nucleotide compound to treat cirrhotic patients infected with hepatitis C.

BACKGROUND OF THE INVENTION

Hepatitis C (HCV) is an RNA single-stranded virus and member of the Hepacivirus genus. Generally, the acute phase of HCV is the first six months following the infection and symptoms may include fatigue, loss of appetite, and jaundice. In some cases, the immune system or drug therapy resolves the infection, but if not, HCV enters the chronic stage. Chronic HCV progression is characterized by inflammation, scarring, and hardening of the liver. Severe scarring and hardening is called cirrhosis. About 20% of people with chronic HCV will experience gradual damage to the liver and progress to cirrhosis in 15-20 years. Approximately 71 million people worldwide are living with chronic HCV infections and approximately 399,000 people die each year from HCV, primarily from cirrhosis and hepatocellular carcinoma.

Cirrhosis can be classified as either compensated or decompensated. Patients with compensated cirrhosis do not necessarily have symptoms related to cirrhosis, but may have asymptomatic esophageal or gastric varices. Patients with decompensated cirrhosis have symptomatic complications related to cirrhosis, including jaundice and symptoms related to portal hypertension including ascites (bloating from fluid build-up in the abdomen), variceal hemorrhage (severe bleeding from enlarged veins in the esophagus and upper stomach), or hepatic encephalopathy (brain disorder that develops when the liver is unable to remove ammonia from the body).

The Child-Turcotte-Pugh (CTP) score has been shown to accurately predict outcomes in patients with cirrhosis and portal hypertension. It consists of five parameters: serum bilirubin, serum albumin, prothrombin time, ascites, and grade of encephalopathy, and based on the sum of points from these parameters, patients are characterized as either A, B, or C. Patients that score an "A" on the CTP scoring system are considered to have mild hepatic impairment and compensated cirrhosis, while patients that score a "B" or "C" on the CTP scoring system are considered to have moderate or severe liver disease, respectively, and decompensated cirrhosis.

The HCV non-structural protein NS5B RNA-dependent RNA polymerase is a key enzyme responsible for initiating and catalyzing viral RNA synthesis, and is therefore a key drug target for the treatment of HCV. Two major subclasses of NS5B inhibitors include nucleoside analogs and non-nucleoside inhibitors (NNIs). Nucleoside analogs are anabolized to active triphosphates that act as alternative substrates for the polymerase. Non-nucleoside inhibitors (NNIs) bind to allosteric regions on the protein. Nucleoside or nucleotide inhibitors mimic natural polymerase substrates and act as chain terminators by inhibiting the initiation of RNA transcription and elongation of a nascent RNA chain.

In December 2013, the first nucleoside NS5B polymerase inhibitor sofosbuvir (Sovaldi®, Gilead Sciences) was approved. Sovaldi® is a uridine phosphoramidate prodrug that is taken up by hepatocytes and undergoes intracellular activation to afford the active metabolite, 2'-deoxy-2'-α-fluoro-β-C-methyluridine-5'-triphosphate.

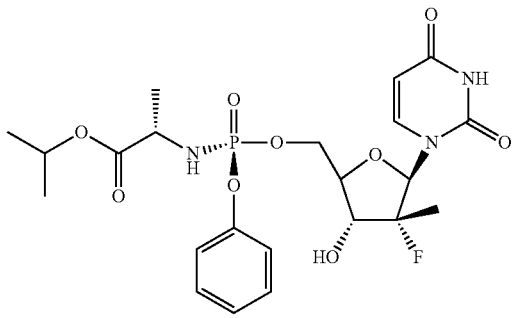

Sovaldi®

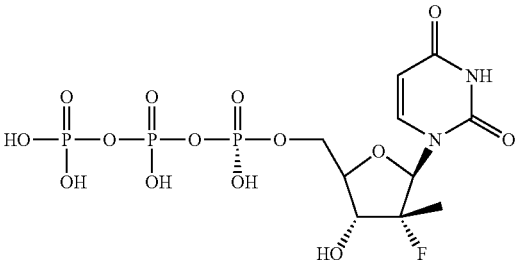

2'-Deoxy-2'-α-fluoro-β-C-methyluridine-5'-triphosphate

Sovaldi® is the first drug that has demonstrated safety and efficacy to treat certain types of HCV infection without the need for co-administration of interferon. Sovaldi® is the third drug with breakthrough therapy designation to receive FDA approval.

In addition to targeting RNA polymerase, other RNA viral proteins may also be targeted, especially in combination therapies. For example, HCV proteins that are additional targets for therapeutic approaches are NS3/4A (a serine protease) and NS5A (a non-structural protein that is an essential component of HCV replicase and exerts a range of effects on cellular pathways).

In 2014, the U.S. FDA approved Harvoni® (ledispasvir, a NS5A inhibitor, and sofosbuvir) to treat chronic hepatitis C virus Genotype 1 infection. Harvoni® is the first combination pill approved to treat chronic HCV Genotype 1 infection. It is also the first approved regimen that does not require administration with interferon or ribavirin in non-cirrhotic patients. In addition, the FDA approved simeprevir (Olysio™) in combination with sofosbuvir (Sovaldi®) as a once-daily, all oral, interferon and ribavirin-free treatment for adults with Genotype 1 HCV infection.

The U.S. FDA also approved AbbVie's VIEKIRA Pak™ in 2014, a multi-pill pack containing dasabuvir (a non-nucleoside NS5B polymerase inhibitor), ombitasvir (a NS5A inhibitor), paritaprevir (a NS3/4A inhibitor), and ritonavir. The VIEKIRA Pak™ can be used with or without the ribavirin to treat Genotype 1 HCV infected patients including patients with compensated cirrhosis. VIEKIRA Pak™ does not require interferon co-therapy.

In July 2015, the U.S. FDA approved Technivie™ and Daklinza™ for the treatment of HCV genotype 4 and HCV Genotype 3, respectively. Technivie™ (Ombitasvir/paritaprevir/ritonavir) was approved for use in combination with ribavirin for the treatment of HCV Genotype 4 in patients without scarring and cirrhosis and is the first option for HCV-4 infected patients who do not require co-administration with interferon. Daklinza™ was approved for use with Sovaldi® to treat HCV Genotype 3 infections. Daklinza™ is the first drug that has demonstrated safety and efficacy in treating HCV Genotype 3 without the need for co-administration of interferon or ribavirin.

In October 2015, the U.S. FDA warned that HCV treatments Viekira Pak and Technivie can cause serious liver injury primarily in patients with underlying advanced liver disease and required that additional information about safety be added to the label.

Other current approved therapies for HCV include interferon alpha-2b or pegylated interferon alpha-2b)(Pegintron®, which can be administered with ribavirin)(Rebetol®, NS3/4A telaprevir (Incivek®, Vertex and Johnson & Johnson), boceprevir (Victrelis™, Merck), simeprevir (Olysio™, Johnson & Johnson), paritaprevir (AbbVie), Ombitasvir (AbbVie), the NNI Dasabuvir (ABT-333), glecaprevir/pibrentasvir (Mavyret®) and Merck's Zepatier™ (a single-tablet combination of the two drugs grazoprevir and elbasvir).

The American Association for the Study of Liver Diseases (AASLD)/Infectious Diseases Society of America (IDSA) recommends combination therapy for treatment-naïve patients infected with HCV Genotype 1a, 1b, 2, 3, or 4 with compensated cirrhosis. A daily fixed-dose of elbasvir/grazoprevir (Zepatier®), glecaprevir/pibrentasvir (Mavyret®), ledipasvir/sofosbuvir (Harvoni®), or sofosbuvir/velpatasvir (Epclusa®) are recommended for patients with GT1a, GT1b, and GT4 HCV infections with compensated cirrhosis. A daily fixed-dose of Epclusa® or Mavyret® is recommended for patients with GT2 or GT3 HCV infections with compensated cirrhosis. The recommended treatment for patients of any genotypic HCV with decompensated cirrhosis is to be referred to a medical practitioner with expertise, ideally a liver transplant expert. Recommended combination therapy for those with decompensated cirrhosis and GT1, GT4, GT5, or GT6 include Harvoni®, Epclusa®, or daclatasvir plus sofosbuvir with doses of ribavirin if the patient is ribavirin eligible. Recommended combination therapy for those with decompensated cirrhosis and GT2 or GT3 include Epclusa® or daclatasvir plus sofosbuvir with doses of ribavirin if the patient is ribavirin eligible.

Mavyret® and other protease inhibitor-containing regimes are generally contraindicated in patients with decompensated cirrhosis due to safety concerns (excessively high plasma levels of the PIs are expected in these patients, which can be liver toxic).

Sovaldi® has been evaluated for the treatment of cirrhotic HCV in the FISSION study and the POSITRON study. The FISSION study evaluated the use of sofosbuvir-ribavirin for 12 weeks in 327 patients with GT1, GT2, or GT3 HCV wherein 20% of the patients were cirrhotic. Among patients with cirrhosis at baseline, only 47% of those administered sofosbuvir-ribavirin had a sustained virologic response. In the POSITRON study, two phase 3 studies in patients with chronic GT2 or GT3 HCV infection were treated with sofosbuvir-ribavirin. In one trial, patients for whom peg-interferon was not an option were enrolled and in the other trial, patients who had not had a response to prior interferon therapy were enrolled. In both studies, response rates were lower among patients with GT3 infection, and among patients with GT3 infection, response rates were lower among those with cirrhosis.

Sovaldi® plus velpatasvir (Epclusa®) for 12 weeks is the only available nucleoside-containing regimen indicated for all 6 common HCV genotypes. The addition of ribavirin to this regimen is required for patients with decompensated cirrhosis, but not for those with compensated cirrhosis. However, emerging data have shown that Sovaldi® plus velpatasvir for 12 weeks had poor response (SVR12=50%) in patients with HCV GT3b and compensated cirrhosis (Wei L. et al. Safety and efficacy of sofosbuvir/velpatasvir in genotype 1-6 HCV-infected patients in China: results from a phase 3 clinical trial. Abs. 637. Hepatology. 2018; 68(1, Suppl): 379A). Similarly, low SVR12 rates were also observed in patients with HCV GT3 and decompensated cirrhosis, despite the doubling of treatment duration to 24 weeks. SVR12 didn't improve until ribavirin was added to the regimen (Curry M P et al. Sofosbuvir and velpatasvir for HCV in patients with decompensated cirrhosis. N Engl J Med. 2015; 373:2618-28.).

In fact, poor responses in GT3 cirrhotic subjects appeared to be the sole reason for the discontinuation of uprifosbuvir (MK-3682), a uridine nucleotide prodrug structurally close to Sovaldi® (Lawitz E, et al. C-BREEZE-2: Efficacy and safety of a two-drug direct-acting antiviral agent regimen ruzasvir 180 mg and uprifosbuvir 450 mg for 12 weeks in adults with chronic hepatitis C virus genotype 1, 2, 3, 4, 5, or 6. Abs. 61. Hepatology. 2017; 66(1, Suppl): 34A-35A). In the C-BREEZE 1 study, the combination of uprifosbuvir and the NSSA inhibitor ruzasvir (MK-8408) was tested in adults with GT1, 2, 3, 4, or 6 HCV, 31% of whom had cirrhosis. The efficacy of the combination was lowest in GT3 where virologic failure was reported in 9 of the 39 GT3 patients, and 6 of the 9 patients were cirrhotic. The C-BREEZE 2 study evaluated the combination of uprifosbuvir and ruzasvir in subjects with GT1-6 HCV where 22% of the participants had compensated cirrhosis. Similar to C-BREEZE 1, the combination therapy was the least effective in GT3, especially in subjects that were GT3 cirrhotic. The overall efficacy (SVR12) in GT3 patients was 76%. An even lower SVR12 rate of 68% was observed in the subset of cirrhotic GT3 patients, whereas SVR12 rate in non-cirrhotic GT3 patients was 80%.

There remains a strong medical need to develop anti-HCV therapies that are safe, effective and well-tolerated in patients that are cirrhotic. More potent direct-acting antivirals could significantly shorten treatment duration and improve compliance and SVR (sustained viral response) rates for patients infected with all HCV genotypes.

It is therefore an object of the present invention to provide compounds, pharmaceutical compositions, methods, and dosage forms to treat and/or prevent infections of HCV in patients that are cirrhotic.

SUMMARY OF THE INVENTION

It has been discovered that the hemi-sulfate salt of Compound 1, which is provided below as Compound 2, exhibits potent antiviral activity in cirrhotic HCV-infected patients as an NSSB inhibitor. Compound 2 is potent in subjects with cirrhotic HCV infections, especially the difficult to treat GT3 infections.

The data comparing the efficacy and pharmacokinetic steady state parameters in cirrhotic and non-cirrhotic patients (Examples 3-4 and FIGS. 6A-6D) clearly demonstrates that Compound 2 maintains efficacy in cirrhotic patients. In fact, the steady-state plasma trough level ($C_\tau$) of metabolite 1-7 after administration of 600 mg of Compound 2 is higher than the $EC_{95}$ for all subjects tested, confirming the equivalent and impressive activity in cirrhotic patients. This data indicates that Compound 2 is a potent prodrug with activity against HCV in subjects with cirrhosis of the liver, and in particular, compensated cirrhosis. The mean HCV RNA change from baseline to 24 hours in patients with GT1, GT2, or GT3 HCV infections with cirrhosis given a 600 mg dose of Compound 2 was 2.4 $\log_{10}$ IU/mL and the mean change from baseline after 7 days of 600 mg/d of Compound 2 resulted in a reduction of 4.6 $\log_{10}$ IU/mL in cirrhotic patients with GT1, GT2, or GT3 infections.

The present invention is thus the use of Compound 2 to treat hepatitis C (HCV) in a cirrhotic host in need thereof, optionally in a pharmaceutically acceptable carrier. In one embodiment, the cirrhotic host has compensated cirrhosis. In another embodiment, the host has decompensated cirrhosis. In one embodiment, the host has Child-Pugh A cirrhosis. In one embodiment, the host has Child-Pugh B or Child-Pugh C cirrhosis.

Compound 2 is referred to as the hemi-sulfate salt of Compound 1, isopropyl((S)-(((2R,3R,4R,5R)-5-(2-amino-6-(methylamino)-9H-purin-9-yl)-4-fluoro-3-hydroxy-4-methyltetrahydrofuran-2-yl)methoxy)(phenoxy)phosphoryl)-L-alaninate. Compound 1 is disclosed in PCT Application No. WO 2016/144918. Compound 2 is disclosed in PCT Application No. WO 2018/144640.

Atea Pharmaceuticals, Inc. has also disclosed β-D-2'-deoxy-2'-α-fluoro-2'-β-C-substituted-2-modified-$N^6$-(mono- and di-methyl) purine nucleotides for the treatment of Flaviviruses in U.S. Pat. Nos. 9,828,410, 10,000,523; 10,005,811; and, 10,239,911; U.S. Application US 2018-0215776; and, PCT Application Nos. WO 2016/144918; WO 2018/048937; and, WO 2018/144640. Atea has also disclosed β-D-2'-deoxy-2'-substituted-4'-substituted-2-$N^6$-substituted-6-aminopurine nucleotides for the treatment of paramyxovirus and orthomyxovirus infections in U.S. Pat. No. 10,202,412 and PCT Application No. WO 2018/009623.

As discussed in Example 3 and Example 4, Compound 2 was evaluated for its safety, pharmacokinetics, and anti-viral activity in cirrhotic and non-cirrhotic subjects with GT1, GT2, or GT3 HCV. No serious adverse events, dose-limiting toxicities or premature discontinuations were observed. A single dose of Compound 2 (600 mg, equivalent to 550 mg of Compound 1) results in a mean maximum HCV RNA reduction of 2.4 $\log_{10}$ IU/mL and a 7-day dosing regimen (600 mg once a day (QD)) results in a mean maximum HCV RNA reduction of 4.5 $\log_{10}$ IU/mL in Child Pugh A cirrhotic subjects with GT1b, GT2, or GT3 HCV infections. An $E_{max}$ model (FIG. 7) shows the clinical observation that 600 mg of Compound 2 QD in cirrhotic patients will produce maximum efficacy by achieving an AUC of metabolite 1-7 that is greater than 2000 ng/mL×h, the AUC predicted to result in a maximum viral load reduction of at least 4 log units.

The weight of Compound 2 in the dosage form described herein is with respect to the salt form unless otherwise specifically indicated. The corresponding dosage of the free form is often given in parenthesis. For example, a 550 mg dose of Compound 1 is clinically equivalent to 600 mg of Compound 2.

Compound 2, as Compound 1, is converted to its corresponding triphosphate nucleotide (Compound 1-6) in the cell, which is the active metabolite and inhibitor of RNA polymerase (see Scheme 1 below). Since Compound 1-6 is produced in the cell and does not leave the cell, it is not measurable in the plasma. However, the 5'-OH metabolite Compound 1-7 (see Scheme 1) is exported from the cell, and therefore is measurable in plasma and acts as a surrogate of the concentration of intracellular active metabolite Compound 1-6.

Scheme 1 provides the metabolic pathway of Compound 1 and Compound 2, which involves the initial de-esterification of the phosphoramidate (metabolite 1-1) to form metabolite 1-2. Metabolite 1-2 is then converted to the $N^6$-methyl-2,6-diaminopurine-5'-monophosphate derivative (metabolite 1-3), which is in turn metabolized to the free 5'-hydroxyl-$N^6$-methyl-2,6-diaminopurine nucleoside (metabolite 1-8) and ((2R,3R,4R,5R)-5-(2-amino-6-oxo-1,6-dihydro-9H-purin-9-yl)-4-fluoro-3-hydroxy-4-methyltetrahydrofuran-2-yl)methyl dihydrogen phosphate as the 5'-monophosphate (metabolite 1-4). Metabolite 1-4 is anabolized to the corresponding diphosphate (metabolite 1-5) and then the active triphosphate derivative (metabolite 1-6). The 5'-triphosphate can be further metabolized to generate 2-amino-9-((2R,3R,4R,5R)-3-fluoro-4-hydroxy-5-(hydroxymethyl)-3-methyltetrahydrofuran-2-yl)-1,9-dihydro-6H-purin-6-one (1-7). Metabolite 1-7 is measurable in plasma and is therefore a surrogate for the active triphosphate (1-6), which is not measurable in plasma.

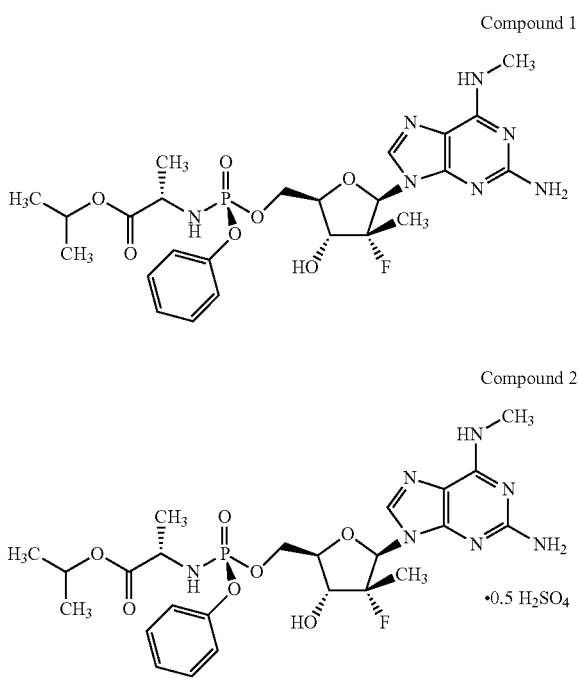

Scheme 1

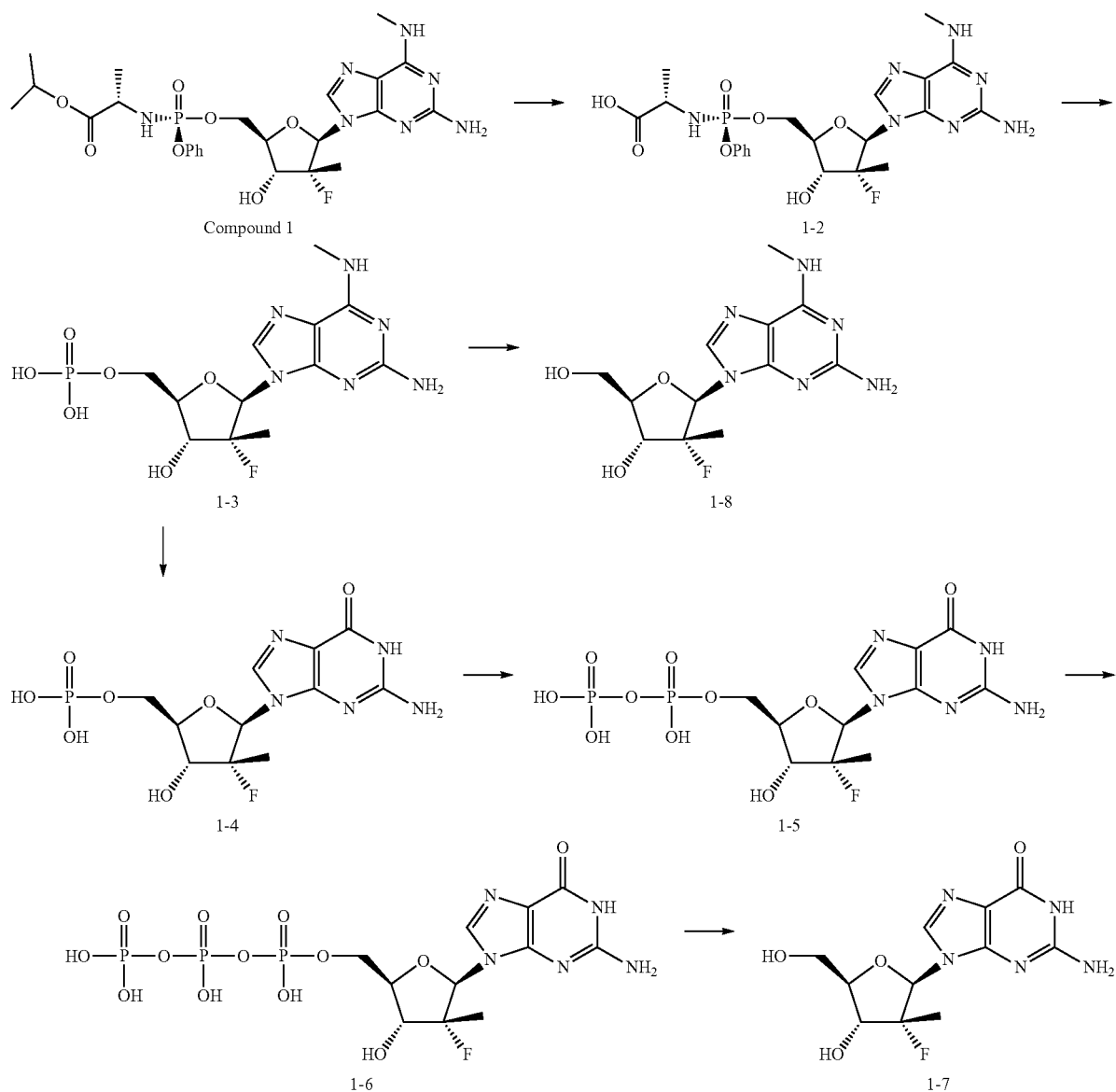

Compounds, methods, dosage forms, and compositions are provided for the treatment of HCV in a cirrhotic host in need thereof wherein the host has cirrhosis of the liver caused by HCV. In certain embodiments, Compound 2 is administered at a dose of at least about 100, 200, 250, 300, 350, 400, 450, 500, 550, 600, 650, 700, 750, 800, 850, 900, 950, or 1000 mg. In certain embodiments, Compound 2 is administered for up to 12 weeks, for up to 10 weeks, for up to 8 weeks, for up to 6 weeks, or for even up to 4 weeks. In alternative embodiments, Compound 2 is administered for at least 4 weeks, for at least 6 weeks, for at least 8 weeks, for at least 10 weeks, or for at least 12 weeks. In certain embodiments, Compound 2 is administered at least once a day or every other day. In one embodiment, Compound 2 is administered to an HCV-positive cirrhotic patient in an amount that achieves at least an HCV RNA reduction of 3 log units, 4 log unit, or 5 log units.

The compounds, compositions, and dosage forms can also be used to treat related conditions in subjects with cirrhosis such as anti-HCV antibody positive and antigen positive conditions, viral-based chronic liver inflammation, liver cancer resulting from advanced hepatitis C (hepatocellular carcinoma (HCC)), chronic or acute hepatitis C, fulminant hepatitis C, chronic persistent hepatitis C and anti-HCV-based fatigue.

The present invention thus includes the following features:
(a) Use of Compound 2 in the manufacture of a medicament for treatment of a hepatitis C virus infection in a cirrhotic patient, for example, a compensated cirrhotic patient;
(b) Compound 2 for use to treat hepatitis C in a cirrhotic patient, for example, a compensated cirrhotic patient, optionally in a pharmaceutically acceptable carrier;
(c) A method for manufacturing a medicament intended for the therapeutic use for treating a hepatitis C virus infection in a cirrhotic patient, for example, a compensated cirrhotic patient, characterized in that Compound 2, or a pharmaceutically acceptable salt, as described herein is used in the manufacture; and (d) A pharmaceutical formulation comprising an effective host-treating amount of Compound 2 with a pharmaceutically acceptable carrier or diluent wherein the host is cirrhotic.

DETAILED DESCRIPTION OF THE INVENTION

Figure 1:
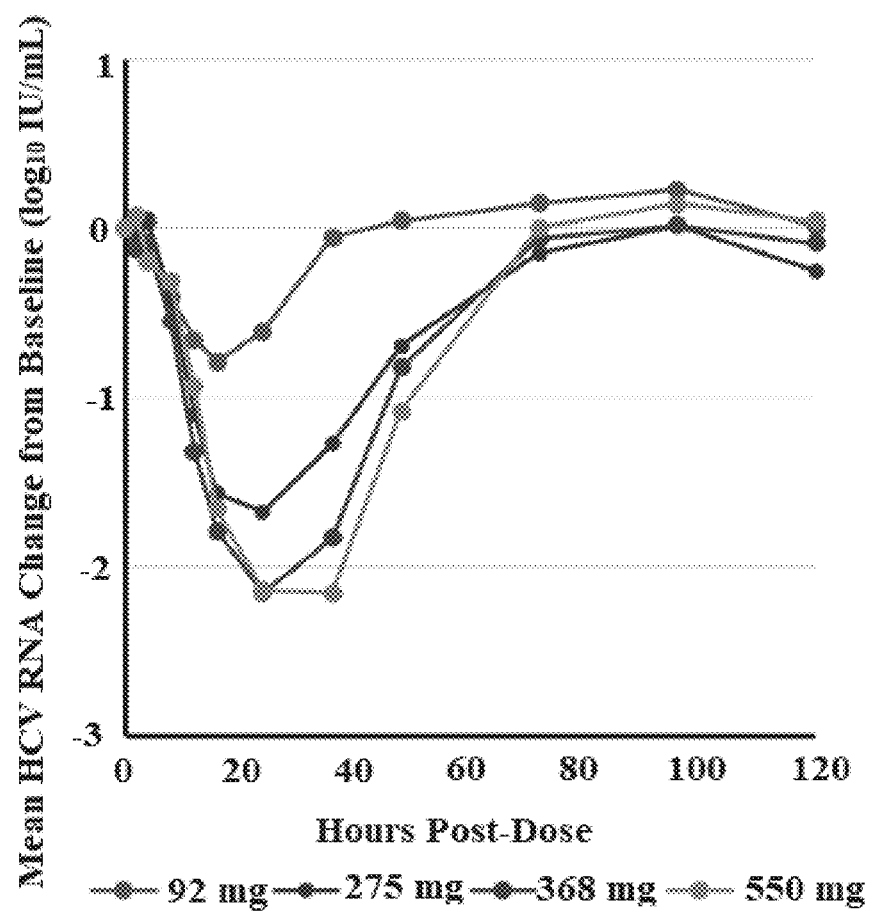
FIG. 1 is a graph demonstrating the mean HCV RNA change from baseline in subjects with non-cirrhotic GT1b HCV infection after a single dose of the Compound 2 equivalent of 92 mg, 275 mg, 368 mg, or 550 mg of Compound 1 as described in Examples 3 and 4. The x-axis is hours measured post dose and the y-axis is mean HCV RNA change from baseline measured in $\log_{10}$ IU/mL.

The invention disclosed herein is a compound, method, composition, and solid dosage form for the treatment of cirrhotic humans and other host animals infected with or exposed to the HCV virus that includes the administration of an effective amount of the hemi-sulfate salt of isopropyl ((S)-(((2R,3R,4R,5R)-5-(2-amino-6-(methylamino)-9H-purin-9-yl)-4-fluoro-3-hydroxy-4-methyltetrahydrofuran-2-yl)methoxy)(phenoxy)phosphoryl)-L-alaninate (Compound 2) as described herein, optionally in a pharmaceutically acceptable carrier. In one embodiment, the cirrhotic host has compensated cirrhosis. In one embodiment, the host has decompensated cirrhosis. In one embodiment, the host has Child-Pugh A cirrhosis. In an alternative embodiment, the host has Child-Pugh B or Child-Pugh C cirrhosis.

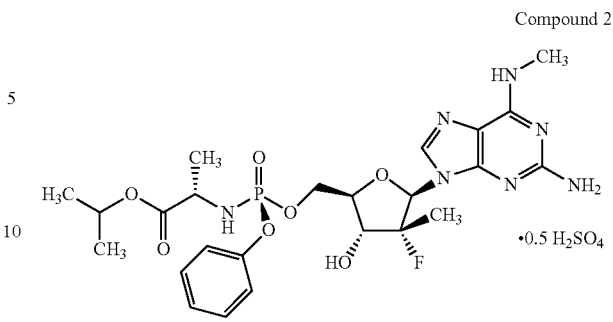

Compound 2

The active compounds and compositions can also be used to treat the range of HCV genotypes in cirrhotic hosts. At least six distinct genotypes of HCV, each of which have multiple subtypes, have been identified globally. Genotypes 1-3 are prevalent worldwide, and Genotypes 4, 5, and 6 are more limited geographically. Genotype 4 is common in the Middle East and Africa. Genotype 5 is mostly found in South Africa. Genotype 6 predominately exists in Southeast Asia.

Although the most common genotype in the United States is Genotype 1, defining the genotype and subtype can assist in treatment type and duration. For example, different genotypes respond differently to different medications and optimal treatment times vary depending on the genotype infection. Within genotypes, subtypes, such as Genotype 1a and Genotype 1b, respond differently to treatment as well. Infection with one type of genotype does not preclude a later infection with a different genotype.

As described in Example 3, Compound 2 is active against GT1, GT2, and GT3 in cirrhotic patients. In one embodiment, Compound 2 is used to treat subjects with cirrhosis of the liver that are infected with HCV Genotype 1, HCV Genotype 2, HCV Genotype 3, HCV Genotype 4, HCV Genotype 5, or HCV Genotype 6. In one embodiment, Compound 2 is used to treat subjects with cirrhosis of the liver infected with HCV Genotype 1a or 1b. In one embodiment, Compound 2 is used to treat subjects with cirrhosis of the liver infected with HCV Genotype 2a or 2b. In one embodiment, Compound 2 is used to treat subjects with cirrhosis of the liver infected with HCV Genotype 3a. In one embodiment, Compound 2 is used to treat subjects with cirrhosis of the liver infected with HCV Genotype 3b. In one embodiment, Compound 2 is used to treat subjects with cirrhosis of the liver infected with HCV Genotype 4a, 4b, 4c, 4d, 4f, 4g/4k, or 4o. In one embodiment, Compound 2 is used to treat subjects with cirrhosis of the liver infected with HCV Genotype 5a or 6a. In one embodiment, Compound 2 is used to treat subjects with cirrhosis of the liver infected with HCV Genotype 6b, 6c, 6d, 6e, 6f, 6g, 6h, 6i, 6j, 6k, 6l, 6m, 6n, 6o, 6p, 6q, 6r, 6s, 6t, or 6u.

In particular, it has been discovered that Compound 2 is active against HCV in subjects that are cirrhotic with GT1, GT2, or GT3 HCV infections.

Compound 2 has S-stereochemistry at the phosphorus atom. In alternative embodiments, Compound 2 can be used in the form of any desired ratio of phosphorus R- and S-enantiomers, including up to pure enantiomers. In some embodiments, Compound 2 is used in a form that is at least 90% free of the opposite enantiomer, and can be at least 98%, 99%, or even 100% free of the opposite enantiomer. Unless described otherwise, an enantiomerically enriched Compound 2 is at least 90% free of the opposite enantiomer.

In addition, in an alternative embodiment, the amino acid of the phosphoramidate can be in the D- or L-configuration, or a mixture thereof, including a racemic mixture.

Unless otherwise specified, the compounds described herein are provided in the β-D-configuration. In an alternative embodiment, the compounds can be provided in a β-L-configuration. Likewise, any substituent group that exhibits chirality can be provided in racemic, enantiomeric, diastereomeric form, or any mixture thereof. Where a phosphoramidate exhibits chirality, it can be provided as an R or S chiral phosphorus derivative or a mixture thereof, including a racemic mixture. All of the combinations of these stereo configurations are alternative embodiments in the invention described herein. In another embodiment, at least one of the hydrogens of Compound 2 (the nucleotide or the hemi-sulfate salt) can be replaced with deuterium.

These alternative configurations include, but are not limited to,

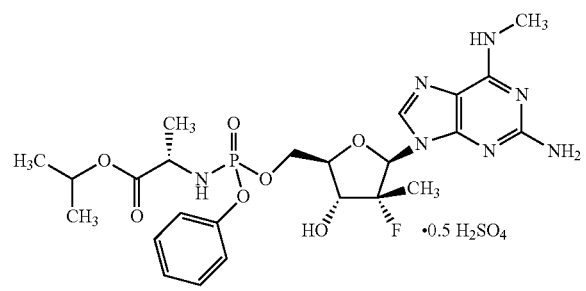

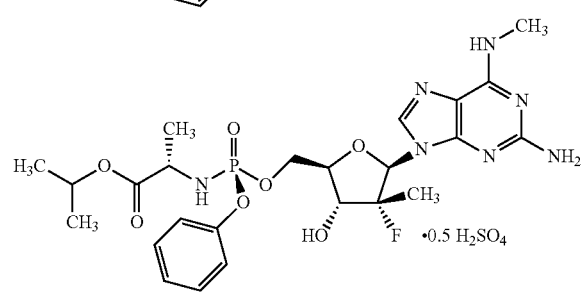

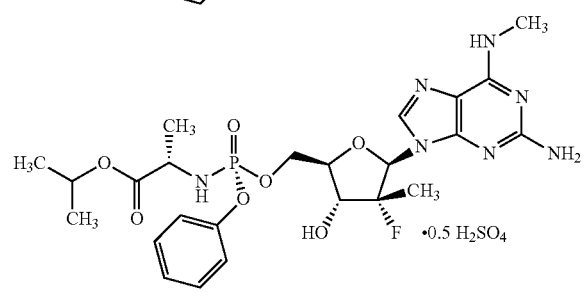

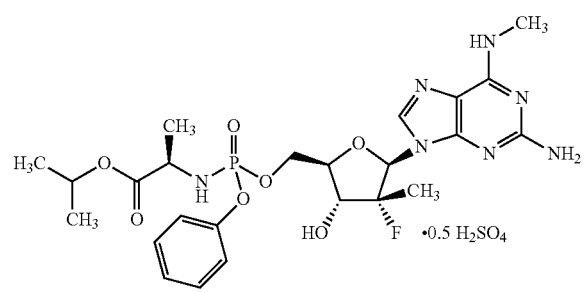

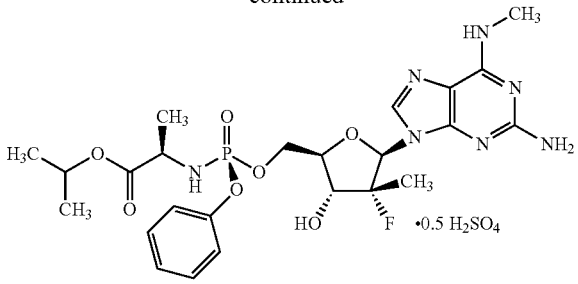

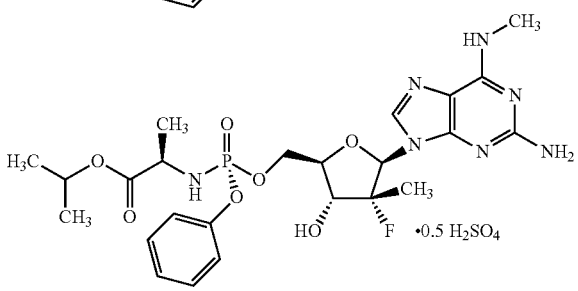

In an alternative embodiment, Compound 2 is administered as an oxalate salt, a sulfate salt, or an HCl salt. Examples of additional alternative pharmaceutically acceptable salts are organic acid addition salts formed with acids, which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including sulfate, nitrate, bicarbonate, and carbonate salts. Alternative pharmaceutically acceptable salts may also be obtained using standard procedures well known in the art, for example by reacting a sufficiently basic compound such as an amine with a suitable acid affording a physiologically acceptable anion. Alkali metal (for example, sodium, potassium, or lithium) or alkaline earth metal (for example calcium) salts of carboxylic acids can also be made.

In an alternative embodiment, Compound 2 is provided as the hemi-sulfate salt of a phosphoramidate of Compound 1 other than the specific phosphoramidate described in the compound illustration. A wide range of phosphoramidates are known to those skilled in the art that include various esters and phospho-esters, any combination of which can be used to provide an active compound as described herein in the form of a hemi-sulfate salt.

I. Hemi-sulfate salt of isopropyl((S)-(((2R,3R,4R,5R)-5-(2-amino-6-(methylamino)-9H-purin-9-yl)-4-fluoro-3-hydroxy-4-methyltetrahydrofuran-2-yl)methoxy)(phenoxy)phosphoryl)-L-alaninate (Compound 2

The active compound of the invention is Compound 2, which can be provided in a pharmaceutically acceptable composition or solid dosage form thereof. In one embodiment, Compound 2 is an amorphous solid. In yet a further embodiment, Compound 2 is a crystalline solid as described in PCT Application WO 2018/144640.

II. Metabolism of Isopropyl((S)-(((2R,3R,4R,5R)-5-(2-amino-6-(methylamino)-9H-purin-9-yl)-4-fluoro-3-hydroxy-4-methyltetrahydrofuran-2-yl)methoxy)(phenoxy)phosphoryl)-L-alaninate (Compound 2)

The metabolism of Compound 1 and Compound 2 involves the production of a 5'-monophosphate and the subsequent anabolism of the N⁶-methyl-2,6-diaminopurine base (1-3) to generate ((2R,3R,4R,5R)-5-(2-amino-6-oxo-1,6-dihydro-9H-purin-9-yl)-4-fluoro-3-hydroxy-4-methyltetrahydrofuran-2-yl)methyl dihydrogen phosphate (1-4) as the 5'-monophosphate. The monophosphate is then further anabolized to the active triphosphate species: the 5'-triphosphate (1-6). The 5'-triphosphate can be further metabolized to generate 2-amino-9-((2R,3R,4R,5R)-3-fluoro-4-hydroxy-5-(hydroxymethyl)-3-methyltetrahydrofuran-2-yl)-1,9-dihydro-6H-purin-6-one (1-7). Alternatively, 5'-monophophate 1-2 can be metabolized to generate the purine base 1-8. The metabolic pathway for isopropyl((S)-(((2R,3R,4R,5R)-5-(2-amino-6-(methylamino)-9H-purin-9-yl)-4-fluoro-3-hydroxy-4-methyltetrahydrofuran-2-yl)methoxy)(phenoxy)phosphoryl)-L-alaninate is illustrated in Scheme 1 (shown above in Scheme 1).

III. Definitions

The term "D-configuration" as used in the context of the present invention refers to the principle configuration which mimics the natural configuration of sugar moieties as opposed to the unnatural occurring nucleosides or "L" configuration. The term "0" or "β anomer" is used with reference to nucleoside analogs in which the nucleoside base is configured (disposed) above the plane of the furanose moiety in the nucleoside analog.

The terms "coadminister" and "coadministration" or combination therapy are used to describe the administration of Compound 2 according to the present invention in combination with at least one other active agent, for example where appropriate at least one additional anti-HCV agent. The timing of the coadministration is best determined by the medical specialist treating the patient. It is sometimes preferred that the agents be administered at the same time. Alternatively, the drugs selected for combination therapy may be administered at different times to the patient. Of course, when more than one viral or other infection or other condition is present, the present compounds may be combined with other agents to treat that other infection or condition as required.

The term "host", as used herein, refers to a unicellular or multicellular organism in which a HCV virus can replicate, including cell lines and animals, and typically a human. The term host specifically refers to infected cells, cells transfected with all or part of a HCV genome, and animals, in particular, primates (including chimpanzees) and humans. In most animal applications of the present invention, the host is a human patient. Veterinary applications, in certain indications, however, are clearly anticipated by the present invention (such as chimpanzees). The host can be for example, bovine, equine, avian, canine, feline, etc.

The term "cirrhosis," as used herein is the late stage, irreversible scarring (fibrosis) of the liver. Signs and symptoms include fatigue, easy bleeding or bruising, loss of appetite, nausea, swelling in the legs, feet or ankles (edema), weight loss, itchy skin, yellow discoloration in the skin and eyes (jaundice), fluid accumulation in the abdomen (ascites), spiderlike blood vessels on your skin, redness in the palms of the hands, confusion, drowsiness and slurred speech (hepatic encephalopathy).

Cirrhosis can be classified as either compensated or decompensated. Patients with compensated cirrhosis do not necessarily have symptoms related to cirrhosis, but may have asymptomatic esophageal or gastric varices. Patients with decompensated cirrhosis have symptomatic complications related to cirrhosis, including jaundice.

The Child-Turcotte-Pugh (CTP) score has been shown to accurately predict outcomes in patients with cirrhosis and portal hypertension. It consists of five parameters: serum bilirubin, serum albumin, prothrombin time, ascites, and grade of encephalopathy, and based on the sum of points from these parameters, patients are characterized as either A, B, or C. Patients that score an "A" on the CTP scoring system are considered to have mild hepatic impairment and compensated cirrhosis, while patients that score a "B" or "C" on the CTP scoring system are considered to have moderate or severe liver disease, respectively, and decompensated cirrhosis.

Isotopic Substitutions

The present invention includes compounds and the use of compound 2 with desired isotopic substitutions of atoms at amounts above the natural abundance of the isotope, i.e., enriched. Isotopes are atoms having the same atomic number but different mass numbers, i.e., the same number of protons but a different number of neutrons. By way of general example and without limitation, isotopes of hydrogen, for example, deuterium ($^2$H) and tritium ($^3$H) may be used anywhere in described structures. Alternatively or in addition, isotopes of carbon, e.g., $^{13}$C and $^{14}$C, may be used. A preferred isotopic substitution is deuterium for hydrogen at one or more locations on the molecule to improve the performance of the drug. The deuterium can be bound in a location of bond breakage during metabolism (an α-deuterium kinetic isotope effect) or next to or near the site of bond breakage (a β-deuterium kinetic isotope effect). Achillion Pharmaceuticals, Inc. (WO/2014/169278 and WO/2014/169280) describes deuteration of nucleotides to improve their pharmacokinetic or pharmacodynamic, including at the 5-position of the molecule.

Substitution with isotopes such as deuterium can afford certain therapeutic advantages resulting from greater metabolic stability, such as, for example, increased in vivo half-life or reduced dosage requirements. Substitution of deuterium for hydrogen at a site of metabolic break-down can reduce the rate of or eliminate the metabolism at that bond. At any position of the compound that a hydrogen atom may be present, the hydrogen atom can be any isotope of hydrogen, including protium ($^1$H), deuterium ($^2$H) and tritium ($^3$H). Thus, reference herein to a compound encompasses all potential isotopic forms unless the context clearly dictates otherwise.

The term "isotopically-labeled" analog refers to an analog that is a "deuterated analog", a "$^{13}$C-labeled analog," or a "deuterated/$^{13}$C-labeled analog." The term "deuterated analog" means a compound described herein, whereby a H-isotope, i.e., hydrogen/protium ($^1$H), is substituted by a H-isotope, i.e., deuterium ($^2$H). Deuterium substitution can be partial or complete. Partial deuterium substitution means that at least one hydrogen is substituted by at least one deuterium. In certain embodiments, the isotope is 90, 95 or 99% or more enriched in an isotope at any location of interest. In some embodiments it is deuterium that is 90, 95 or 99% enriched at a desired location. Unless indicated to the contrary, the deuteration is at least 80% at the selected location. Deuteration of the nucleoside can occur at any replaceable hydrogen that provides the desired results.

IV. Method of Treatment or Prophylaxis

Treatment, as used herein, refers to the administration of Compound 2 to a host that is infected with HCV, for example a human, wherein the host has cirrhosis of the liver caused by HCV. In one embodiment, the cirrhotic host has compensated cirrhosis. In an alternative embodiment, the cirrhotic host has decompensated cirrhosis. In one embodiment, the host has Child-Pugh A cirrhosis. In an alternative embodiment, the host has Child-Pugh B or Child-Pugh C cirrhosis.

The invention is directed to a method of treatment or prophylaxis of a hepatitis C virus, including drug resistant and multi-drug resistant forms of HCV and related disease states, conditions, or complications of a cirrhotic HCV infection, including related hepatotoxicities, as well as other conditions that are secondary to a cirrhotic HCV infection, such as weakness, loss of appetite, weight loss, breast enlargement (especially in men), rash (especially on the palms), difficulty with clotting of blood, spider-like blood vessels on the skin, confusion, coma (encephalopathy), buildup of fluid in the abdominal cavity (ascites), esophageal varices, portal hypertension, variceal hemorrhage, kidney failure, enlarged spleen, decrease in blood cells, anemia, thrombocytopenia, jaundice, and hepatocellular cancer, among others. The method comprises administering to a host in need thereof, typically a human, with an effective amount of Compound 2 as described herein, optionally in combination with at least one additional bioactive agent, for example, an additional anti-HCV agent, further in combination with a pharmaceutically acceptable carrier additive and/or excipient.

In yet another aspect, the present invention is a method for prevention or prophylaxis of a cirrhotic HCV infection or a disease state or related or follow-on disease state, condition or complication of a cirrhotic HCV infection, including related hepatotoxicities, weakness, loss of appetite, weight loss, breast enlargement (especially in men), rash (especially on the palms), difficulty with clotting of blood, spider-like blood vessels on the skin, confusion, coma (encephalopathy), buildup of fluid in the abdominal cavity (ascites), esophageal varices, portal hypertension, variceal hemorrhage, kidney failure, enlarged spleen, decrease in blood cells, anemia, thrombocytopenia, jaundice, and hepatocellular (liver) cancer, among others, said method comprising administering to a patient at risk with an effective amount Compound 2 as described above in combination with a pharmaceutically acceptable carrier, additive, or excipient, optionally in combination with another anti-HCV agent. In another embodiment, the active compounds of the invention can be administered to a patient after a hepatitis-related liver transplantation to protect the new organ.

V. Pharmaceutical Compositions and Dosage Forms

In an aspect of the invention, pharmaceutical compositions according to the present invention comprise an anti-HCV virus effective amount of Compound 2 as described herein to treat a cirrhotic HCV infection, optionally in combination with a pharmaceutically acceptable carrier, additive, or excipient, further optionally in combination or alternation with at least one other active compound. In one embodiment, the invention includes a solid dosage form of Compound 2 in a pharmaceutically acceptable carrier.

In an aspect of the invention, pharmaceutical compositions according to the present invention comprise an anti-HCV effective amount of Compound 2 described herein to treat a cirrhotic HCV infection, optionally in combination with a pharmaceutically acceptable carrier, additive, or excipient, further optionally in combination with at least one other antiviral agent, such as an anti-HCV agent.

The invention includes pharmaceutical compositions that include an effective amount to treat a cirrhotic hepatitis C virus infection of Compound 2 of the present invention or prodrug, in a pharmaceutically acceptable carrier or excipient.

One of ordinary skill in the art will recognize that a therapeutically effective amount will vary with the infection or condition to be treated, its severity, the treatment regimen to be employed, the pharmacokinetic of the agent used, as well as the patient or subject (animal or human) to be treated, and such therapeutic amount can be determined by the attending physician or specialist.

Compound 2 according to the present invention can be formulated in a mixture with a pharmaceutically acceptable carrier. In general, it is preferable to administer the pharmaceutical composition in orally-administrable form, an in particular, a solid dosage form such as a pill or tablet. Certain formulations may be administered via a parenteral, intravenous, intramuscular, topical, transdermal, buccal, subcutaneous, suppository, or other route, including intranasal spray. Intravenous and intramuscular formulations are often administered in sterile saline. One of ordinary skill in the art may modify the formulations to render them more soluble in water or another vehicle, for example, this can be easily accomplished by minor modifications (salt formulation, esterification, etc.) that are well within the ordinary skill in the art. It is also well within the routineers' skill to modify the route of administration and dosage regimen of Compound 2 in order to manage the pharmacokinetics of the present compounds for maximum beneficial effect in patients, as described in more detail herein.

The amount of Compound 2 included within the therapeutically active formulation according to the present invention is an effective amount to achieve the desired outcome according to the present invention, for example, for treating the cirrhotic HCV infection, reducing the likelihood of a cirrhotic HCV infection or the inhibition, reduction, and/or abolition of cirrhotic HCV or its secondary effects, including disease states, conditions, and/or complications which occur secondary to cirrhotic HCV. In general, a therapeutically effective amount of the present compound in a pharmaceutical dosage form may range from about 0.001 mg/kg to about 100 mg/kg per day or more, more often, slightly less than about 0.1 mg/kg to more than about 25 mg/kg per day of the patient or considerably more, depending upon the compound used, the condition or infection treated and the route of administration. Compound 2 is often administered in amounts ranging from about 0.1 mg/kg to about 15 mg/kg per day of the patient, depending upon the pharmacokinetic of the agent in the patient. This dosage range generally produces effective blood level concentrations of active compound which may range from about 0.001 to about 100, about 0.05 to about 100 micrograms/cc of blood in the patient.

Often, to treat, prevent or delay the onset of these infections and/or to reduce the likelihood of a cirrhotic HCV virus infection, or a secondary disease state, condition or complication of HCV, Compound 2 will be administered in a solid dosage form in an amount ranging from about 250 micrograms up to about 800 milligrams or more at least once a day, for example, at least about 5, 10, 20, 25, 50, 75, 100, 150, 200, 250, 300, 350, 400, 450, 500, 550, 600, 650, 700, 750, 800, 850, 900, 950, or 1000 milligrams or more, once, twice, three, or up to four times a day according to the direction of the healthcare provider. Compound 2 is often administered orally, but may be administered parenterally, topically, or in suppository form, as well as intranasally, as a nasal spray or as otherwise described herein. More generally, Compound 2 can be administered in a tablet, capsule, injection, intravenous formulation, suspension, liquid, emulsion, implant, particle, sphere, cream, ointment, suppository, inhalable form, transdermal form, buccal, sublingual, topical, gel, mucosal, and the like.

When a dosage form herein refers to a milligram weight dose, it refers to the amount of Compound 2 (i.e., the weight of the hemi-sulfate salt) unless otherwise specified to the contrary.

In certain embodiments, the pharmaceutical composition is in a dosage form that contains from about 1 mg to about 2000 mg, from about 10 mg to about 1000 mg, from about 100 mg to about 800 mg, from about 200 mg to about 600 mg, from about 300 mg to about 500 mg, or from about 400 mg to about 450 mg of Compound 2 in a unit dosage form. In certain embodiments, the pharmaceutical composition is in a dosage form, for example in a solid dosage form, that contains up to about 10, about 50, about 100, about 125, about 150, about 175, about 200, about 225, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, or about 1000 mg or more of Compound 2 in a unit dosage form. In one embodiment, Compound 2 is administered in a dosage form that delivers at least about 300 mg. In one embodiment, Compound 2 is administered in a dosage form that delivers at least about 400 mg. In one embodiment, Compound 2 is administered in a dosage form that delivers at least about 450 mg. In one embodiment, Compound 2 is administered in a dosage form that delivers at least about 500 mg. In one embodiment, Compound 2 is administered in a dosage form that delivers at least about 550 mg. In one embodiment, Compound 2 is administered in a dosage form that delivers at least about 600 mg. In one embodiment, Compound 2 is administered in a dosage form that delivers at least about 650 mg. In one embodiment, Compound 2 is administered in a dosage form that delivers at least about 700 mg. In one embodiment, Compound 2 is administered in a dosage form that delivers at least about 750 mg. In one embodiment, Compound 2 is administered in a dosage form that delivers at least about 800 mg. In one embodiment, Compound 2 is administered in a dosage form that delivers at least about 850 mg. In one embodiment, Compound 2 is administered in a dosage form that delivers at least about 900 mg. In one embodiment, Compound 2 is administered in a dosage form that delivers at least about 950 mg. In one embodiment, Compound 2 is administered in a dosage form that delivers at least about 1000 mg. In certain embodiments, Compound 2 is administered at least once, twice, or three times a day for up to 12 weeks. In certain embodiments, Compound 2 is administered at least once, twice, or three times a day for up to 10 weeks. In certain embodiments, Compound 2 is administered at least once, twice, or three times a day for up to 8 weeks. In certain embodiments, Compound 2 is administered at least once, twice, or three times a day for up to 6 weeks. In certain embodiments, Compound 2 is administered at least once, twice, or three times a day for up to 4 weeks. In certain embodiments, Compound 2 is administered at least once, twice, or three times a day for at least 4 weeks. In certain embodiments, Compound 2 is administered at least once, twice, or three times a day for at least 6 weeks. In certain embodiments, Compound 2 is administered at least once, twice, or three times a day for at least 8 weeks. In certain embodiments, Compound 2 is administered at least once, twice, or three times a day for at least 10 weeks. In certain embodiments, Compound 2 is administered at least once, twice, or three times a day for at least 12 weeks. In certain embodiments, Compound 2 is administered at least once, twice, or three times a day for up to 12 weeks, up to 10 weeks, up to 8 weeks, up to 6 weeks, or up to 4 weeks. In certain embodiments, Compound 2 is administered at least every other day for at least 4 weeks, at least 6 weeks, at least 8 weeks, at least 10 weeks, or at least 12 weeks. In one embodiment, at least about 1000 mg of Compound 2 is administered at least once, twice, or three times a day for up to 6 weeks. In one embodiment, at least about 900 mg of Compound 2 is administered at least once, twice, or three times a day for up to 6 weeks. In one embodiment, at least about 800 mg of Compound 2 is administered at least once, twice, or three times a day for up to 6 weeks. In one embodiment, at least about 700 mg of Compound 2 is administered at least once, twice, or three times a day for up to 6 weeks. In one embodiment, at least about 600 mg of Compound 2 is administered at least once, twice, or three times a day for up to 6 weeks. In one embodiment, at least about 550 mg of Compound 2 is administered at least once, twice, or three times a day for up to 6 weeks. In one embodiment, at least about 500 mg of Compound 2 is administered at least once, twice, or three times a day for up to 6 weeks. In one embodiment, at least about 450 mg of Compound 2 is administered at least once, twice, or three times a day for up to 6 weeks. In one embodiment, at least about 400 mg of Compound 2 is administered at least once, twice, or three times a day for up to 6 weeks. In one embodiment, at least about 350 mg of Compound 2 is administered at least once, twice, or three times a day for up to 6 weeks. In one embodiment, at least 300 mg of Compound 2 is administered at least once, twice, or three times a day for up to 6 weeks. In one embodiment, at least 200 mg of Compound 2 is administered at least once, twice, or three times a day for up to 6 weeks. In one embodiment, at least 100 mg of Compound 2 is administered at least once, twice, or three times a day for up to 6 weeks.

In certain embodiments, a dose of approximately 600 mg of Compound 2 administered to a cirrhotic GT1 HCV infected patient results in at least a 3 log, 4 log, or 5 log HCV RNA reduction.

In certain embodiments, a dose of approximately 600 mg of Compound 2 administered to a cirrhotic GT2 HCV infected patient results in at least a 3 log, 4 log, or 5 log HCV RNA reduction. In certain embodiments, a dose of approximately 600 mg of Compound 2 administered to a cirrhotic GT3 HCV infected patient results in at least a 3 log, 4 log, or 5 log HCV RNA reduction.

In the case of the co-administration of Compound 2 in combination with another anti-HCV compound as otherwise described herein, the amount of Compound 2 according to the present invention to be administered in ranges from about 0.01 mg/kg of the patient to about 800 mg/kg or more of the patient or considerably more, depending upon the second agent to be co-administered and its potency against the virus, the condition of the patient and severity of the disease or infection to be treated and the route of administration. The other anti-HCV agent may for example be administered in amounts ranging from about 0.01 mg/kg to about 800 mg/kg. Examples of dosage amounts of the second active agent are amounts ranging from about 250 micrograms up to about 750 mg or more at least once a day, for example, at least about 5, 10, 20, 25, 50, 75, 100, 150, 200, 250, 300, 350, 400, 450, 500, 600, 700, 800, 850, 900, 9050, or 1000 milligrams or more, up to four times a day. In certain preferred embodiments, Compound 2 may be often administered in an amount ranging from about 0.5 mg/kg to about 50 mg/kg or more (usually up to about 100 mg/kg), generally depending upon the pharmacokinetic of the two agents in the patient. These dosage ranges generally produce effective blood level concentrations of active compound in the patient.

For purposes of the present invention, a prophylactically or preventive effective amount of the compositions according to the present invention falls within the same concentration range as set forth above for therapeutically effective amount and is usually the same as a therapeutically effective amount.

Administration of Compound 2 may range from continuous (intravenous drip) to several oral or intranasal administrations per day (for example, Q.I.D.) or transdermal administration and may include oral, topical, parenteral, intramuscular, intravenous, sub-cutaneous, transdermal (which may include a penetration enhancement agent), buccal, and suppository administration, among other routes of administration. Enteric coated oral tablets may also be used to enhance bioavailability of the compounds for an oral route of administration. The most effective dosage form will depend upon the bioavailability/pharmacokinetic of the particular agent chosen as well as the severity of disease in the patient. Oral dosage forms are particularly preferred, because of ease of administration and prospective favorable patient compliance.

To prepare the pharmaceutical compositions according to the present invention, a therapeutically effective amount of Compound 2 according to the present invention is often intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs, and solutions, suitable carriers and additives including water, glycols, oils, alcohols, flavoring agents, preservatives, coloring agents, and the like may be used. For solid oral preparations such as powders, tablets, capsules, and for solid preparations such as suppositories, suitable carriers and additives including starches, sugar carriers, such as dextrose, manifold, lactose, and related carriers, diluents, granulating agents, lubricants, binders, disintegrating agents, and the like may be used. If desired, the tablets or capsules may be enteric-coated or sustained release by standard techniques. The use of these dosage forms may significantly enhance the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents, and the like may be employed.

Liposomal suspensions (including liposomes targeted to viral antigens) may also be prepared by conventional methods to produce pharmaceutically acceptable carriers. This may be appropriate for the delivery of free nucleosides, acyl/alkyl nucleosides or phosphate ester pro-drug forms of the nucleoside compounds according to the present invention.

In typical embodiments according to the present invention, Compound 2 and the compositions described are used to treat, prevent or delay a cirrhotic HCV infection or a secondary disease state, condition or complication of cirrhotic HCV.

VI. Combination and Alternation Therapy

It is well recognized that drug-resistant variants of viruses can emerge after prolonged treatment with an antiviral agent. Drug resistance sometimes occurs by mutation of a gene that encodes for an enzyme used in viral replication. The efficacy of a drug against a cirrhotic HCV infection may be prolonged, augmented, or restored by administering the compound in combination or alternation with another, and perhaps even two or three other, antiviral compounds that induce a different mutation or act through a different pathway from that of the principle drug. Alternatively, the pharmacokinetic, biodistribution, half-life, or other parameter of the drug may be altered by such combination therapy (which may include alternation therapy if considered concerted). Since the disclosed Compound 2 is an NSSB polymerase inhibitor, it may be useful to administer the compound to a host in combination with, for example a (1) Protease inhibitor, such as an NS3/4A protease inhibitor;
(2) NSSA inhibitor;
(3) Another NSSB polymerase inhibitor;
(4) NSSB non-substrate inhibitor;
(5) Interferon alfa-2a, which may be pegylated or otherwise modified, and/or ribavirin;
(6) Non-substrate-based inhibitor;
(7) Helicase inhibitor;
(8) Antisense oligodeoxynucleotide (S-ODN);
(9) Aptamer;
(10) Nuclease-resistant ribozyme;
(11) iRNA, including microRNA and SiRNA;
(12) Antibody, partial antibody or domain antibody to the virus, or
(13) Viral antigen or partial antigen that induces a host antibody response.

Non limiting examples of anti-HCV agents that can be administered in combination with Compound 2 of the invention, alone or with multiple drugs from this lists, are (i) protease inhibitors such as telaprevir (Incivek®), boceprevir (Victrelis™), simeprevir (Olysio™), paritaprevir (ABT-450), glecaprevir (ABT-493), ritonavir (Norvir), ACH-2684, AZD-7295, BMS-791325, danoprevir, Filibuvir, GS-9256, GS-9451, MK-5172, Setrobuvir, Sovaprevir, Tegobuvir, VX-135, VX-222, and, ALS-220;
(ii) NS5A inhibitor such as ACH-2928, ACH-3102, IDX-719, daclatasvir, ledispasvir, velpatasvir (Epclusa), elbasvir (MK-8742), grazoprevir (MK-5172), Ombitasvir (ABT-267), ruzasvir (MK-8408), ravidasvir, pibrentasvir, and coblopasvir (KW-136);
(iii) NS5B inhibitors such as AZD-7295, Clemizole, dasabuvir (Exviera), ITX-5061, PPI-461, PPI-688, sofosbuvir (Sovaldi®), MK-3682, and mericitabine;
(iv) NS5B inhibitors such as ABT-333, and MBX-700;
(v) Antibody such as GS-6624;
(vi) Combination drugs such as Harvoni (ledipasvir/sofosbuvir); Viekira Pak (ombitasvir/paritaprevir/ritonavir/dasabuvir); Viekirax (ombitasvir/paritaprevir/ritonavir); G/P (paritaprevir and glecaprevir); Technivie (ombitasvir/paritaprevir/ritonavir), Epclusa (sofosbuvir/velpatasvir), Zepatier (elbasvir and grazoprevir), and Mavyret (glecaprevir/pibrentasvir).

If Compound 2 is administered to treat advanced hepatitis C virus leading to liver cancer, in one embodiment, the compound can be administered in combination or alternation with another drug that is typically used to treat hepatocellular carcinoma (HCC), for example, as described by Andrew Zhu in "New Agents on the Horizon in Hepatocellular Carcinoma" Therapeutic Advances in Medical Oncology, V 5(1), January 2013, 41-50. Examples of suitable compounds for combination therapy where the host has or is at risk of HCC include anti-angiogenic agents, sunitinib, brivanib, linifanib, ramucirumab, bevacizumab, cediranib, pazopanib, TSU-68, lenvatinib, antibodies against EGFR, mTor inhibitors, MEK inhibitors, and histone decetylace inhibitors.

EXAMPLES

General Methods $^1$H, $^{19}$F and $^{31}$P NMR spectra were recorded on a 400 MHz Fourier transform Brucker spectrometer. Spectra were obtained DMSO-$d_6$ unless stated otherwise. The spin multiplicities are indicated by the symbols s (singlet), d (doublet), t (triplet), m (multiplet) and, br (broad). Coupling constants (J) are reported in Hz. The reactions were generally carried out under a dry nitrogen atmosphere using Sigma-Aldrich anhydrous solvents. All common chemicals were purchased from commercial sources.

The following abbreviations are used in the Examples:
AUC: Area under the Curve
$C_{max}$: Maximum concentration of the drug achieved in plasma
DCM: Dichloromethane
EtOAc: Ethyl acetate
EtOH: Ethanol
HPLC: High pressure liquid chromatography
NaOH: Sodium hydroxide
$Na_2SO_4$: Sodium sulphate (anhydrous)
MeCN: Acetonitrile
$MeNH_2$: Methylamine
MeOH: Methanol
$Na_2SO_4$: Sodium sulfate
$NaHCO_3$: Sodium bicarbonate
$NH_4Cl$: Ammonium chloride
$NH_4OH$: Ammonium hydroxide
PE: Petroleum ether
$Ph_3P$: Triphenylphosphine
QD: once daily
RH: relative humidity
Silica gel (230 to 400 mesh, Sorbent)
t-BuMgCl: t-Butyl magnesium chloride
$T_{max}$: Time at which $C_{max}$ is achieved
THF: Tetrahydrofuran (THF), anhydrous
TP: Triphosphate Example 1. Synthesis of Compound 1

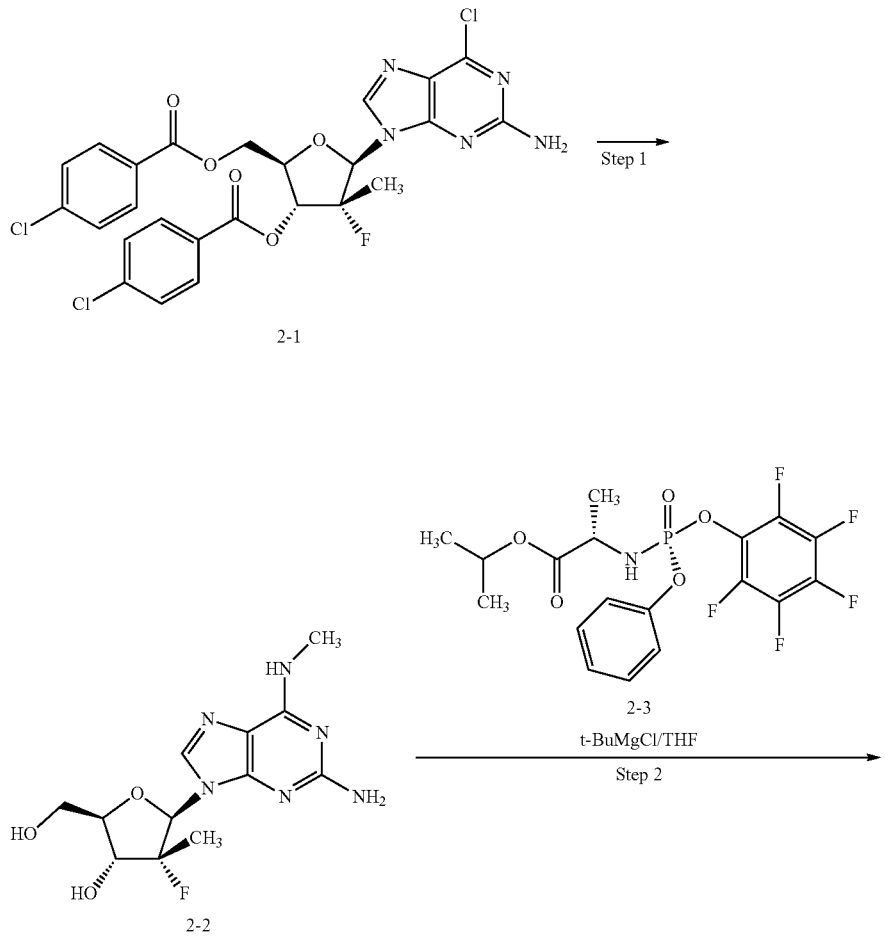

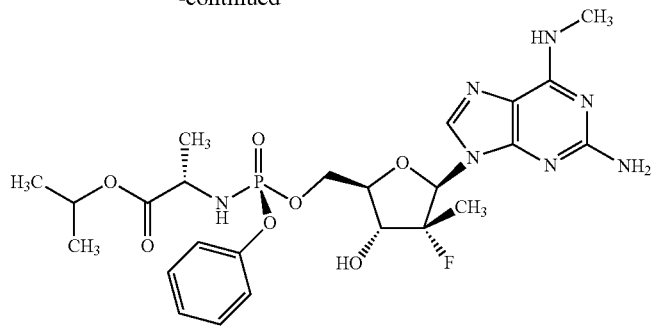

Compound 1

Step 1: Synthesis of (2R,3R,4R,5R)-5-(2-Amino-6-(methylamino)-9H-purin-9-yl)-4-fluoro-2-(hydroxymethyl)-4-methyltetrahydrofuran-3-ol (2-2)

A 50 L flask was charged with methanol (30 L) and stirred at 10±5° C. $NH_2CH_3$ (3.95 Kg) was slowly ventilated into the reactor at 10±5° C. Compound 2-1 (3.77 kg) was added in batches at 20±5° C. and stirred for 1 hour to obtain a clear solution. The reaction was stirred for an additional 6-8 hours, at which point HPLC indicated that the intermediate was less than 0.1% of the solution. The reactor was charged with solid NaOH (254 g), stirred for 30 minutes and concentrated at 50±5° C. (vacuum degree: −0.095). The resulting residue was charged with EtOH (40 L) and re-slurried for 1 hour at 60° C. The mixture was then filtered through celite and the filter cake was re-slurried with EtOH (15 L) for 1 hour at 60° C. The filtrate was filtered once more, combined with the filtrate from the previous filtration, and then concentrated at 50±5° C. (vacuum degree: −0.095). A large amount of solid was precipitated. EtOAc (6 L) was added to the solid residue and the mixture was concentrated at 50±5° C. (vacuum degree: −0.095). DCM was then added to the residue and the mixture was re-slurried at reflux for 1 hour, cooled to room temperature, filtered, and dried at 50±5° C. in a vacuum oven to afford compound 2-2 as an off-white solid (1.89 Kg, 95.3%, purity of 99.2%).

Analytic Method for Compound 2-2: The purity of compound 2-2 (15 mg) was obtained using an Agilent 1100 HPLC system with a Agilent Poroshell 120 EC-C18 4.6*150 mm 4-Micron column with the following conditions: 1 mL/min flow rate, read at 254 nm, 30° C. column temperature, 15 μL injection volume, and a 31 minute run time. The sample was dissolved in acetonitrile-water (20:80) (v/v). The gradient method is shown below.

| Time (min) | A % (0.05 TFA in water) | B % (Acetonitrile) |
| --- | --- | --- |
| 0 | 95 | 5 |
| 8 | 80 | 20 |
| 13 | 50 | 50 |
| 23 | 5 | 95 |
| 26 | 5 | 95 |
| 26.1 | 95 | 5 |
| 31 | 95 | 5 |

Step 2: Synthesis of isopropyl((S)-(((2R,3R,4R,5R)-5-(2-Amino-6-(methylamino)-9H-purin-9-yl)-4-fluoro-3-hydroxy-4-methyltetrahydrofuran-2-yl)methoxy)(phenoxy)phosphoryl)-L-alaninate (Compound 1)

Compound 2-2 and compound 2-3 (isopropyl ((perfluorophenoxy)(phenoxy)phosphoryl)-L-alaninate) were dissolved in THF (1 L) and stirred under nitrogen. The suspension was then cooled to a temperature below −5° C. and a 1.7 M solution of t-BuMgCl solution (384 mL) was slowly added over 1.5 hours while a temperature of 5-10° C. was maintained. A solution of $NH_4Cl$ (2 L) and water (8 L) was added to the suspension at room temperature followed by DCM. The mixture was stirred for 5 minutes before a 5% aqueous solution of $K_2CO_3$ (10 L) was added and the mixture was stirred for 5 additional minutes before filtering through diatomite (500 g). The diatomite was washed with DCM and the filtrate was separated. The organic phase was washed with a 5% aqueous $K_2CO_3$ solution (10 L×2), brine (10 L×3), and dried over $Na_2SO_4$ (500 g) for approximately 1 hour. Meanwhile, this entire process was repeated 7 times in parallel and the 8 batches were combined. The organic phases were filtered and concentrated at 45±5° C. (vacuum degree of 0.09 Mpa). EtOAc was added and the mixture was stirred for 1 hour at 60° C. and then at room temperature for 18 hours. The mixture was then filtered and washed with EtOAc (2 L) to afford crude Compound 1. The crude material was dissolved in DCM (12 L), heptane (18 L) was added at 10-20° C., and the mixture was allowed to stir for 30 minutes at this temperature. The mixture was filtered, washed with heptane (5 L), and dried at 50±5° C. to afford pure Compound 1 (1650 g, 60%).

Analytic Method for Compound 1: The purity of Compound 1 (25 mg) was obtained using an Agilent 1100 HPLC system with a Waters XTerra Phenyl 5 μm 4.6*250 mm column with the following conditions: 1 mL/min flow rate, read at 254 nm, 30° C. column temperature, 15 μL injection volume, and a 25 minute run time. The sample was dissolved in acetonitrile-water (50:50) (v/v). The gradient method is shown below.

| Time (min) | A % (0.1% $H_3PO_4$ in water) | B % (Acetonitrile) |
| --- | --- | --- |
| 0 | 90 | 10 |
| 20 | 20 | 80 |
| 20.1 | 90 | 10 |
| 25 | 90 | 10 |

Example 2. Synthesis of Amorphous Compound 2

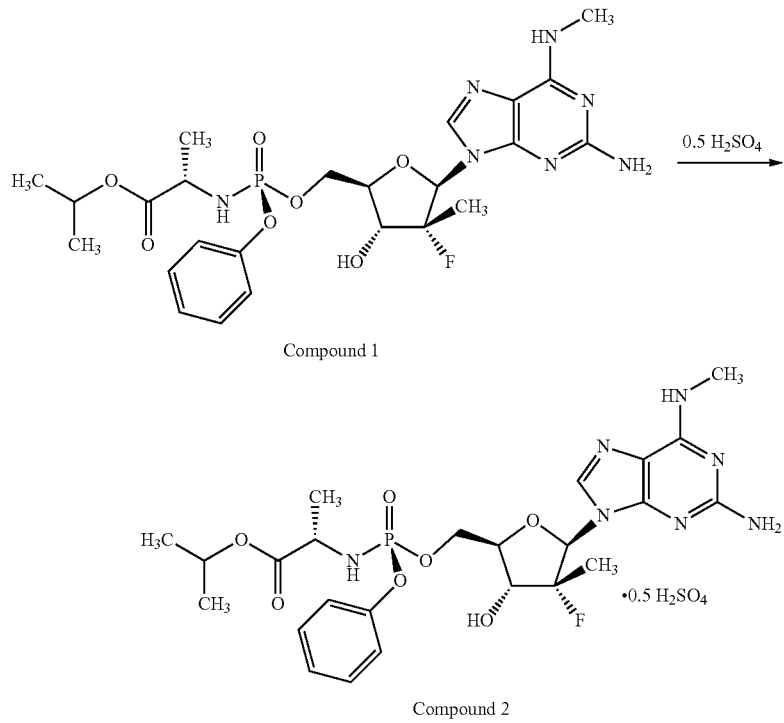

A 250 mL flask was charged with MeOH (151 mL) and the solution was cooled to 0-5° C. A concentrated solution of H$_2$SO$_4$ was added dropwise over 10 minutes. A separate flask was charged with Compound 1 (151 g) and acetone (910 mL), and the H$_2$SO$_4$/MeOH solution was added dropwise at 25-30° C. over 2.5 hours. A large amount of solid was precipitated. After the solution was stirred for 12-15 hours at 25-30° C., the mixture was filtered, washed with MeOH/acetone (25 mL/150 mL), and dried at 55-60° C. in vacuum to afford Compound 2 (121 g, 74%).

Analytic Method for Compound 2: The purity of Compound 2 was obtained using an Agilent 1100 HPLC system with a Waters XTerra Phenyl 5 μm 4.6*250 mm column with the following conditions: 1 mL/min flow rate, read at 254 nm, 30° C. column temperature, 10 μL injection volume, and a 30 minute run time. The sample was dissolved in ACN:water (90:10, v/v). The Gradient method for separation is shown below. R$_t$ (min) of Compound 2 was approximately 12.0 minutes.

| Time (min) | 0.1% H$_3$PO$_4$ in Water (A) % | Acetonitrile (B) % |
| --- | --- | --- |
| 0 | 90 | 10 |
| 20 | 20 | 80 |
| 20.1 | 90 | 10 |
| 30 | 90 | 10 |

$^1$HNMR: (400 MHz, DMSO-d$_6$): δ 8.41 (br, 1H), 7.97 (s, 1H), 7.36 (t, J=8.0 Hz, 2H), 7.22 (d, J=8.0 Hz, 2H), 7.17 (t, J=8.0 Hz, 1H), 6.73 (s, 2H), 6.07 (d, J=8.0 Hz, 1H), 6.00 (dd, J=12.0, 8.0 Hz, 1H), 5.81 (br, 1H), 4.84-4.73 (m, 1H), 4.44-4.28 (m, 3H), 4.10 (t, J=8.0 Hz, 2H), 3.85-3.74 (m, 1H), 2.95 (s, 3H), 1.21 (s, J=4.0 Hz, 3H), 1.15-1.10 (m, 9H).

Compound 2 was further characterized by eye, $^1$HNMR, $^{13}$CNMR, $^{19}$FNMR, MS, HPLC, and XRPD as described in PCT Application WO 2018/144640.

Example 3. Three-Part Study to Evaluate Safety/Tolerability, Pharmacokinetics (PK), and Anti-Viral Activity of Compound 2

A three-part study was conducted with Compound 2 to evaluate safety/tolerability, pharmacokinetics (PK), and anti-viral activity. The three parts included: 1) the administration of multiple doses of up to 600 mg of Compound 2 (equivalent to 550 mg of Compound 1) once daily (QD) for 7 days in NC (non-cirrhotic) GT1 HCV-infected patients (Part C); 2) the administration of 600 mg of Compound 2 (equivalent to 550 mg of Compound 1) QD for 7 days in NC GT3 HCV-infected patients (Part D); and, 3) the administration of 600 mg of Compound 2 (equivalent to 550 mg of Compound 1) QD for 7 days in a cohort of Child-Pugh A (CPA) cirrhotic patients with either GT1, GT2, or GT3 HCV infections (Part E). Doses were administered as the Compound 2 salt base. The free base Compound 1 equivalent is often given in parenthesis.

Part C was a randomized, double-blind, placebo-controlled MAD study divided into three cohorts. Subjects were given 150 mg, 300 mg, or 600 mg of Compound 2 or placebo for 7 days in the fasting state. The dose escalation only proceeded following satisfactory review of the data. Part D and Part E were open-labeled studies where patients received a dose of 600 mg of Compound 2 (equivalent to 550 mg of Compound 1) for 7 days in the fasting state.

HCV-infected patients were treatment-naïve with HCV RNA ≥5 log 10 IU/mL. HCV RNA was quantified using COBAS® AmpliPrep TaqMAN® v2.0 with LLQ of 15 IU/mL. Plasma drug levels were measured using LC-MS/MS. Baseline HCV RNA averaged >6 logs in all cohorts of patients administered 500 mg of Compound 2. Cirrhosis was confirmed by prior liver biopsy or Fibroscan >12.5 kPa. The mean baseline Fibroscan was 6.3, 6.8, and 17.6 kPa in patients administered 600 mg equivalent of Compound 2 in Part C, Part D, and Part E, respectively. Mean ages of enrolled subjects were 44, 39, and 56 years in the non-cirrhotic GT1b 600 mg dose cohort, non-cirrhotic GT3 cohort, and the cirrhotic cohort, respectively.

Part A and Part B were previously conducted and described in WO 2018/144640. Part A and Part B were single ascending dose (SAD) studies. In Part A, healthy subjects were given up to 400 mg of Compound 2 (equivalent to 367 mg of Compound 1) and in Part B, GT1 NC HCV-infected subjects were given single doses of up to 600 mg of Compound 2 (equivalent to 550 mg of Compound 1).

Example 4. Results of Study of Compound 2

No serious adverse events (AEs), dose-limiting toxicities, or premature discontinuations were reported. Compound 2 was well tolerated up to the highest doses tested (600 mg salt form) for seven days. The only pattern observed was a higher incidence of mostly low-grade lipid abnormalities (cholesterol and triglyceride increase) in subjects receiving Compound 2 compared to placebo. However, this observation is consistent with previously published data showing rapid increase in lipids with HCV clearance upon initiation of DAA therapy in HCV-infected subjects. In addition, there were no findings suggestive of liver injury. ALT/AST values decreased over time during the treatment period in subjects receiving Compound 2. Finally, there were no other clinically relevant, dose-related patterns upon analysis of AEs, laboratory parameters, ECGs and vital signs.

In part B, a single dose of the Compound 2 equivalent of 92 mg, 275 mg, 368 mg, or 550 mg of Compound 1 was administered to non-cirrhotic GT1b HCV-infected subjects separated into dosing cohorts (n=3 for each cohort) to determine the mean maximum reduction of HCV RNA, the results of which are shown in FIG. 1 and Table 1. A single dose of 600 mg of Compound 2 (equivalent to 550 mg of Compound 1) administered to non-cirrhotic GT1b HCV-infected subjects (n=3) resulted in a mean maximum HCV RNA reduction of 2.3 $\log_{10}$ IU/mL, with individual maximum HCV RNA reductions of 2.1, 2.3, and 2.6 $\log_{10}$ IU/mL in this cohort.

TABLE 1

HCV RNA Change from Baseline in GT1b HCV Patients after a Single Dose of Compound 2

| Dosing Cohort (Compound 2 Equivalent of Compound 1) | Mean (Individual) Max Reduction ($\log_{10}$ IU/ml) |
|---|---|
| 92 mg | 0.8 (0.6, 0.8, 0.9) |
| 275 mg | 1.7 (1.1, 1.8, 2.2) |
| 368 mg | 2.2 (1.8, 2.2, 2.6) |
| 550 mg | 2.3 (2.1, 2.3, 2.6) |

Figure 2:
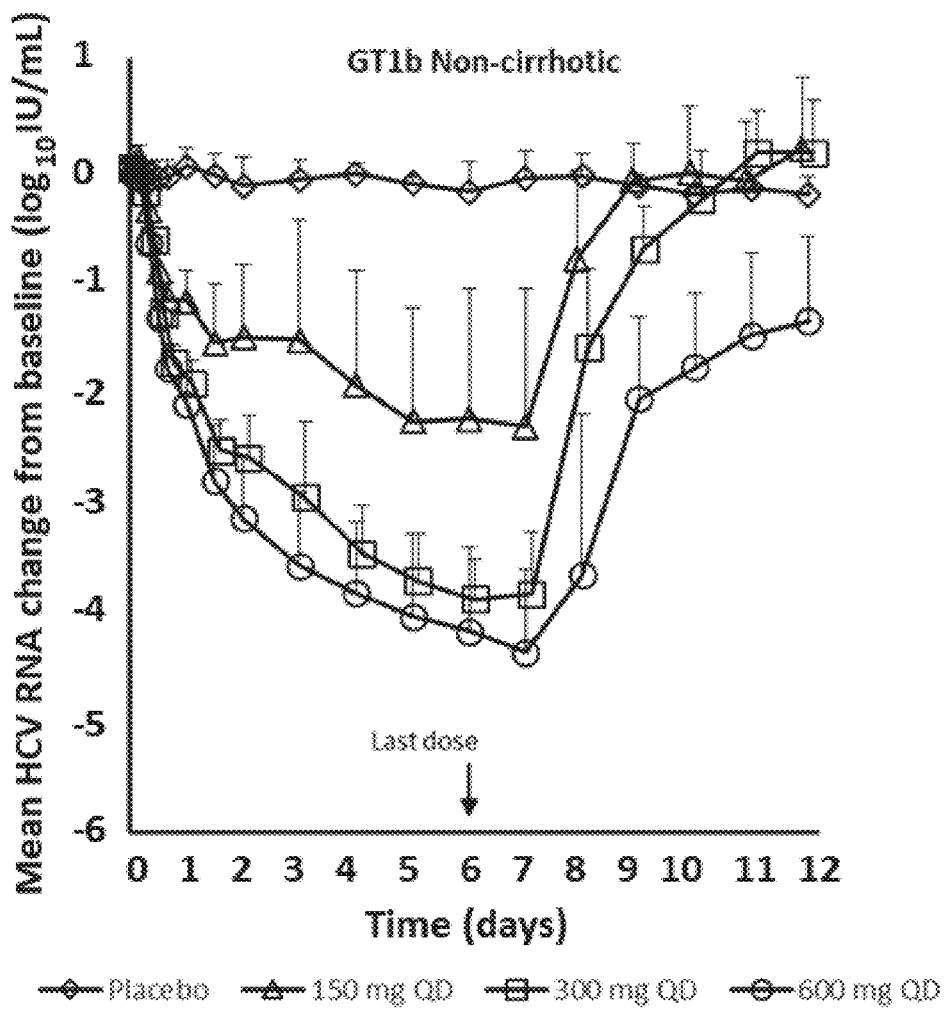
FIG. 2 is a graph demonstrating the mean HCV RNA change from baseline in subjects with non-cirrhotic GT1b HCV infection following 7 days QD of dosing with Compound 2 as described in Examples 3 and 4. The x-axis is days measured post first-dose and the y-axis is mean HCV RNA change from baseline measured in $\log_{10}$ IU/mL.

In Part C, dose-related antiviral activity was observed 7 days after dosing with a mean maximum HCV RNA reduction up to 4.4 $\log_{10}$ IU/mL in non-cirrhotic GT1b HCV-infected subjects (n=6). 50% of subjects achieved HCV RNA <LOQ. FIG. 2 is a graph of the mean HCV RNA change from baseline in subjects given placebo, 150 mg, 300 mg, or 600 mg of Compound 2 once daily (QD). The mean maximum reduction was observed following 7 days of dosing in the three cohorts given 150 mg, 300 mg, or 600 mg of Compound 2 once daily (QD).

In Part D, potent antiviral activity was observed in non-cirrhotic GT3 HCV-infected subjects (n=6) with a mean maximum HCV RNA reduction of 4.5 $\log_{10}$ IU/mL. The mean HCV RNA reduction was 2.4 $\log_{10}$ IU/mL after the first dose of 600 mg of Compound 2 (equivalent to 550 mg of Compound 1) and one subject achieved HCV RNA <LOQ within four days after the first dose.

Figure 3:
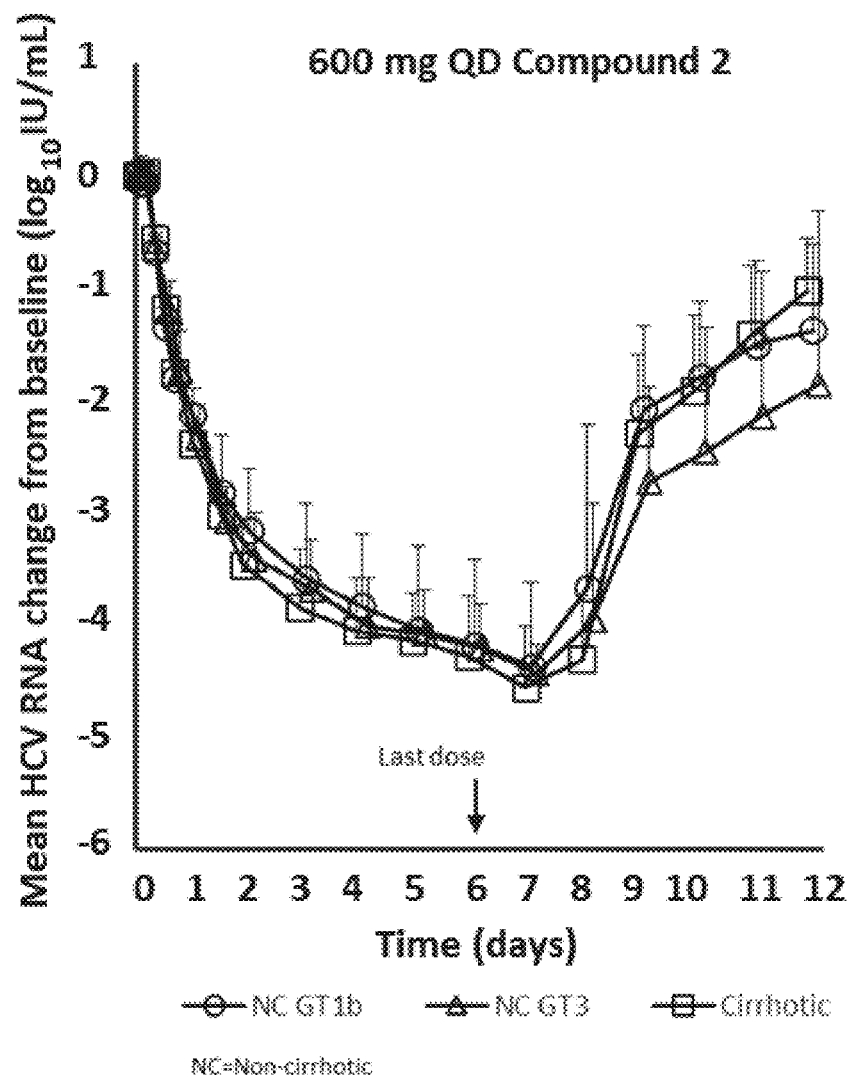
FIG. 3 is graph comparing the mean HCV RNA change from baseline in subjects with non-cirrhotic GT1 HCV infection, subjects with non-cirrhotic GT3 HCV infection, and subjects with cirrhotic HCV infection following doses of 600 mg/day QD of Compound 2 (equivalent to 550 mg of Compound 1) as described in Examples 3 and 4. As shown in the graph, subjects with cirrhosis of the liver exhibited mean HCV RNA change that were similar to subjects with non-cirrhosis of the liver. The x-axis is days measured post first-dose and the y-axis is mean HCV RNA change from baseline measured in $\log_{10}$ IU/mL.

Antiviral activity in the CPA cirrhotic HCV-infected subjects of Part E was similar to non-cirrhotic GT1b and GT3 cohorts. In Part E, the mean maximum HCV RNA reduction of cirrhotic HCV infected patients was 4.6 $\log_{10}$ IU/mL. Mean HCV RNA changes from baseline in these populations are presented in FIG. 3. For comparison, the curves for the ascending dose cohorts (Part C, non-cirrhotic GT1b HCV-infected patients) are shown in FIG. 2 and the curves for all 600 mg QD cohorts (Parts C/D/E) are included in FIG. 3. Metabolite 1-7 antiviral activity observed in each cohort is summarized in Table 4A, Table 4B, and Table 4C.

Figure 4A:
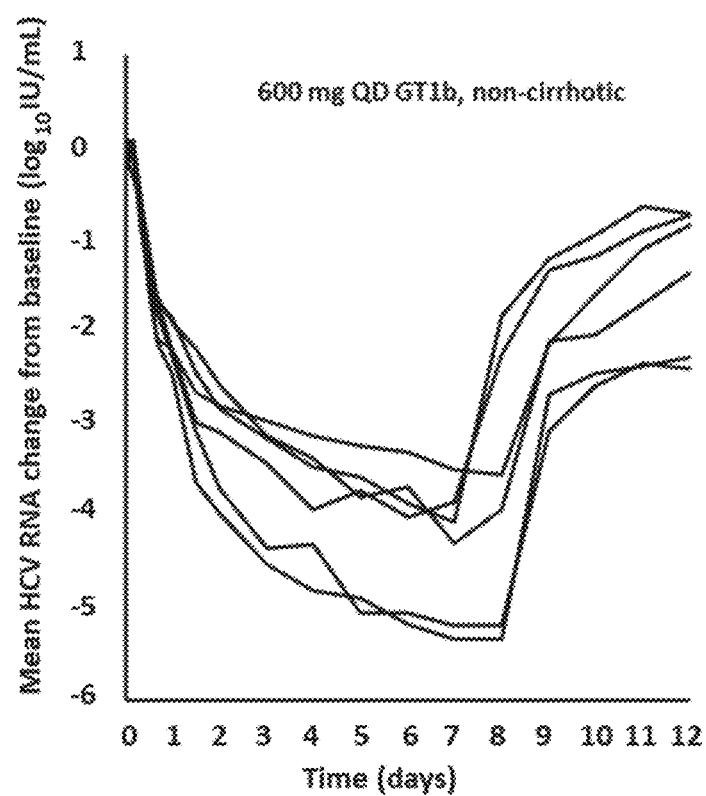
FIG. 4A is a graph of the individual HCV RNA change from baseline in subjects with non-cirrhotic GT1b HCV infection following doses of 600 mg/day QD of Compound 2 (equivalent to 550 mg of Compound 1) as described in Examples 3 and 4. The x-axis is days measured post first-dose and the y-axis is HCV RNA change from baseline measured in $\log_{10}$ IU/mL.
Figure 4B:
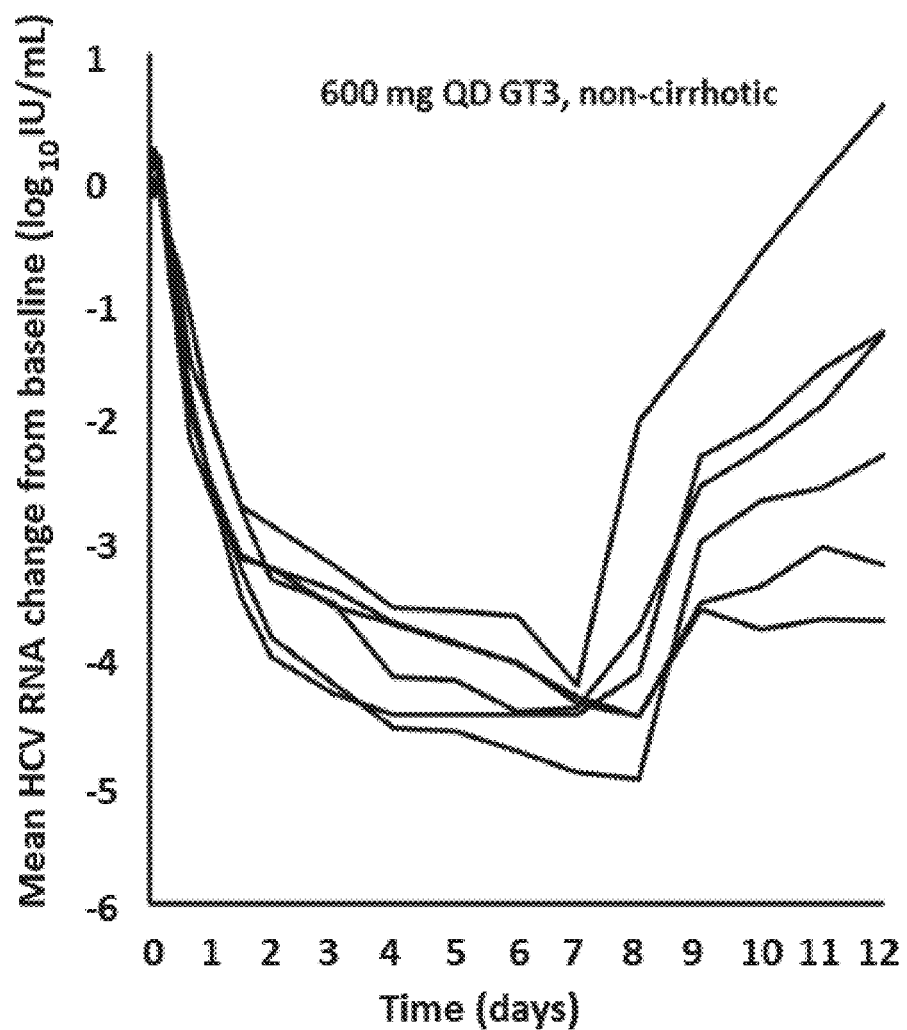
FIG. 4B is a graph of the individual HCV RNA change from baseline in subjects with non-cirrhotic GT3 HCV infection following doses of 600 mg/day QD of Compound 2 (equivalent to 550 mg of Compound 1) as described in Examples 3 and 4. The x-axis is days measured post first-dose and the y-axis is HCV RNA change from baseline measured in $\log_{10}$ IU/mL.
Figure 4C:
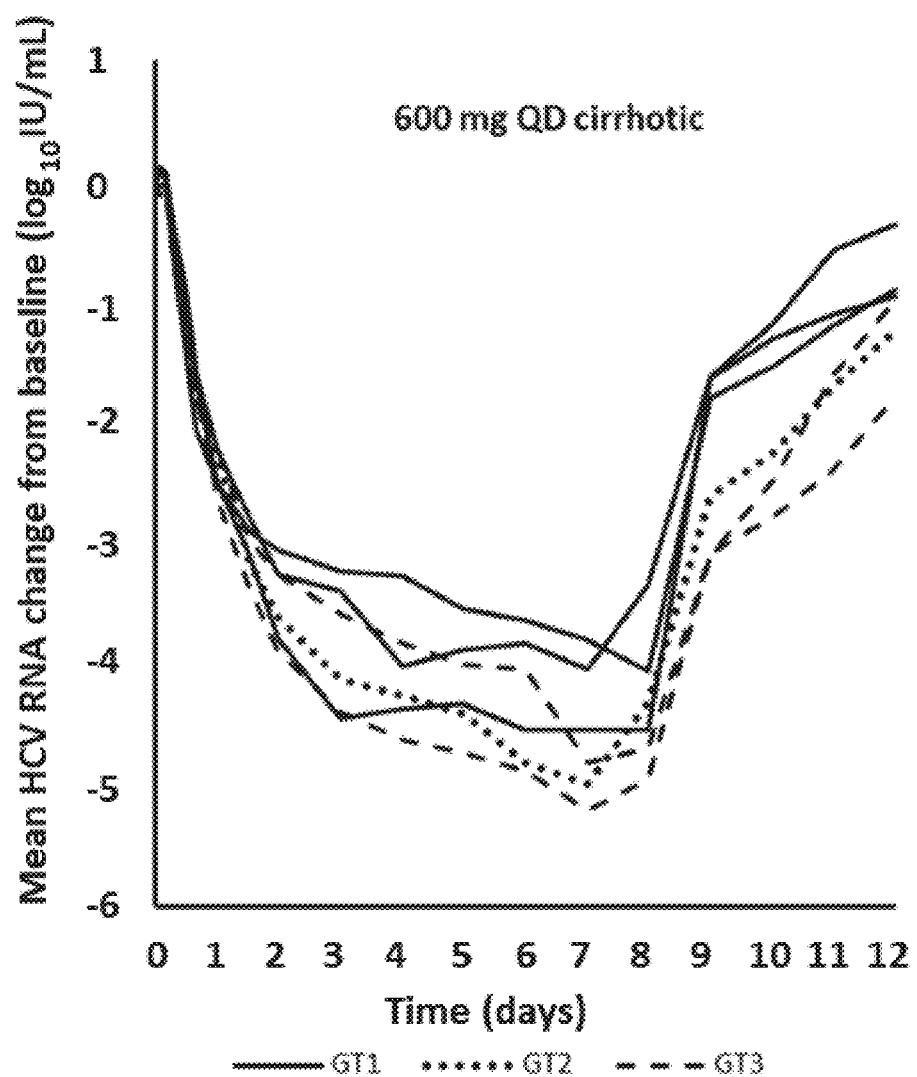
FIG. 4C is a graph of the individual HCV RNA change from baseline in subjects with cirrhotic GT1, GT2, or GT3 HCV infection following doses of 600 mg/day QD of Compound 2 (equivalent to 550 mg of Compound 1) as described in Examples 3 and 4. The x-axis is days measured post first-dose and the y-axis is HCV RNA change from baseline measured in $\log_{10}$ IU/mL.

The mean maximum HCV RNA change for Part C, Part D, and Part E is shown in Table 2. FIGS. 4A-4C are graphs comparing the mean maximum reduction of non-cirrhotic subjects with GT1 HCV infection from Part C, non-cirrhotic subjects with GT3 HCV infection from Part D, and cirrhotic subjects with GT1/GT2/GT3 HCV from Part E. The mean maximum reduction following 7 days of dosing was similar for subjects, regardless of whether the subject was infected with GT1 or GT3 HCV and regardless of whether the subject was cirrhotic or non-cirrhotic. A summary of the antiviral activity among all of these cohorts is shown in Table 2 and Table 3. A profound early viral response in cirrhotic subjects was observed, leading to a 2.4 and 2.2 $\log_{10}$ HCV RNA reduction for GT1 and GT3 HCV subjects, respectively, within the first 24 hours. Five subjects receiving the 600 mg QD dose of metabolite 1-7 (3 subjects in Part C (50%) and 1 subject each in Parts D and E (17%)) achieved HCV RNA levels below the lower limit of quantitation in the study.

TABLE 2

Maximum HCV RNA Change in Part B, Part C, Part D, and Part E

| | | Part C | | | Part D | Part E |
|---|---|---|---|---|---|---|
| Endpoint, $\log_{10}$ IU/mL | Placebo N = 6 | 150 mg/day Compd 2 N = 6 | 300 mg/day Compd 2 N = 6 | 600 mg/day Compd 2 N = 6 | 600 mg/day Compd 2 N = 6 | 600 mg/day Compd 2 N = 6 |
| Mean ± SD HCV RNA change from baseline to 24 h | 0.0 ± 0.2 | 1.2 ± 0.3 | 1.9 ± 0.2 | 2.1 ± 0.2 | 2.3 ± 0.3 | 2.4 ± 0.2 |

TABLE 2-continued

Maximum HCV RNA Change in Part B, Part C, Part D, and Part E

| | | Part C | | | Part D | Part E |
|---|---|---|---|---|---|---|
| Endpoint, log$_{10}$ IU/mL | Placebo N = 6 | 150 mg/day Compd 2 N = 6 | 300 mg/day Compd 2 N = 6 | 600 mg/day Compd 2 N = 6 | 600 mg/day Compd 2 N = 6 | 600 mg/day Compd 2 N = 6 |
| Mean ± SD HCV RNA maximum change from baseline | 0.4 ± 0.1 (0.2 – 0.5)* | 2.6 ± 1.1 (1.5 – 3.7)* | 4.0 ± 0.4 (3.5 – 4.4)* | 4.4 ± 0.7 (3.7 – 5.1)* | 4.5 ± 0.3 (4.1 – 5.0)* | 4.6 ± 0.5 |
| Individual HCV RNA maximum change from baseline | 0.3, 0.3, 0.4, 0.4, 0.5, 0.6 | 1.7, 1.8, 1.8, 2.7, 3.0, 4.5 | 3.4, 3.7, 3.9 4.2, 4.2, 4.5 | 3.5, 4.0, 4.1 4.3, 5.2, 5.3 | 4.2, 4.4, 4.4, 4.5, 4.5, 5.0 | GT1b: 4.0, 4.1, 4.5 GT2: 4.8 GT3: 5.1, 5.2 |

*95% C.I.

TABLE 3

Summary of Antiviral Activity of Compound 2 in Part C, Part D, and Part E for 600 mg of Compound 2

| Dosing Cohort | Mean Reduction After 24 hours (log$_{10}$ IU/mL) | Mean (Individual) Max Reduction (log$_{10}$ IU/mL) | HCV RNA < LOQ (15 IU/mL) |
|---|---|---|---|
| GT1, non-cirrhotic (n = 6) | 2.1 | 4.4 (3.5, 4.0. 4.1, 4.3, 5.2, 5.3) | 3/6 |
| GT3, non-cirrhotic (n = 6) | 2.4 | 4.5 (4.2, 4.4, 4.5, 4.5, 5.0) | 1/6 |
| GT1, Child-Pugh A (n = 3) | 2.4 | 4.2 (4.0, 4.1, 4.5) | 1/3 |
| GT3, Child-Pugh A (n = 1) | 2.2 | 4.8 (n = 1) | 0/1 |

Compound 1, the free base of Compound 2, was rapidly and well-absorbed with estimated fraction absorbed approximating 50% based on urine recovery. After repeated QD administrations for seven days in a fasted state, Compound 1 was quickly absorbed followed by rapid metabolic activation.

Following daily dosing for 7 days in Part C, Compound 1 exhibited a short half-life and did not accumulate over time. Plasma exposure of Compound 1 was slightly more than dose proportional from 150 mg to 300 mg and mostly dose proportional thereafter. While plasma peak and total exposure of metabolite 1-7 was dose proportional from 150 to 300 mg and less than dose proportional from 300 mg to 600 mg, trough levels of metabolite 1-7 were mostly dose proportional in the studied dose range. Based on metabolite 1-7 trough levels, steady state PK was essentially reached after the third or fourth dose. The formation of metabolite 1-7 peaked at approximately 6 hours after dosing and metabolite 1-7 exhibited a long half-life (-13-30 h) which supports once a day (QD) dosing. The long half-life resulted in the desired higher metabolite 1-7 trough (50%-60%) upon reaching steady state. (Active triphosphate 1-6 is not measurable in plasma since it does not leave the cell, and therefore 1-7, which is measurable is plasma, acts as a surrogate for triphosphate 1-6 and reflects intracellular active triphosphate).

Steady state of metabolite 1-7 concentrations was reached by day 3 or 4 in NC subjects and by day 5 in the subjects with cirrhosis. Overall, mild hepatic impairment did not significantly impact the PK of Compound 2 based on plasma exposures. No food effect on total and trough exposure of metabolite 1-7 was observed.

Figure 5:
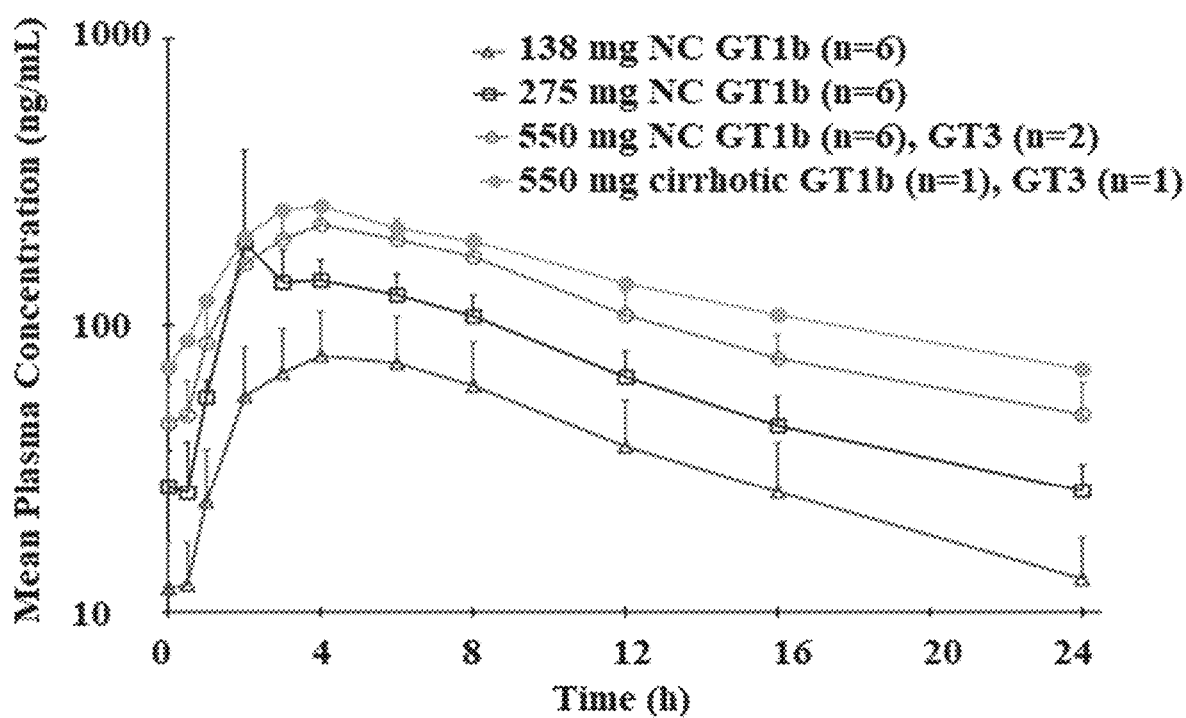
FIG. 5 is the mean plasma concentration-time profile of metabolite 1-7 in GT1/GT3 HCV-infected cirrhotic and non-cirrhotic subjects. The GT1-infected non-cirrhotic subjects were given the Compound 2 equivalent of either 138 mg/d, 275 mg/d, or 550 mg/d QD of Compound 1, the GT3-infected non-cirrhotic subjects were given 600 mg/d QD of Compound 2 (550 mg/d of Compound 1), and the GT1/GT3-infected cirrhotic subjects were given 600 mg of Compound 2 QD (550 mg/d of Compound 1) as described in Examples 3 and 4. The x-axis is time measured in hours and the y-axis is mean plasma concentration measured in ng/mL.

FIG. 5 is a graph of the mean plasma concentration-time profile of metabolite 1-7 at steady-state comparing non-cirrhotic subjects with GT1 HCV infection given the Compound 2 equivalent of 138 mg/d QD of Compound 1, non-cirrhotic subjects with GT1 HCV infection given the Compound 2 equivalent of 275 mg/d QD of Compound 1, non-cirrhotic subjects with GT3 HCV infection given 600 mg of Compound 2 (equivalent to 550 mg of Compound 1), and cirrhotic subjects with GT1 or GT3 HCV infections given 600 mg of Compound 2 (equivalent to 550 mg of Compound 1). Plasma levels of metabolite 1-7 were measured using LC-MS/MS.

Tables 4A, 4B, and 4C shows the mean PK results of subjects enrolled in the study. As shown in Tables 4A-4C and FIG. 5, the PK of metabolite 1-7 is similar in non-cirrhotic and cirrhotic subjects.

TABLE 4A $C_{max}$ and $T_{max}$ for Compound 1 and Metabolite 1-7 at Day 1 and Steady State (SS)

| Analyte | Part | Dose (n) (mg/d) | $C_{max}$ (ng/mL) Day 1 | $C_{max}$ (ng/mL) SS | $T_{max}$ (h) Day 1 | $T_{max}$ (h) SS |
|---|---|---|---|---|---|---|
| Compd 1 | C | 150 (6) | 573 ± 280 | 462 ± 409 | 0.5 (0.5-1.0) | 1.0 (0.5-1.0) |
| | | 300 (6) | 2277 ± 893 | 1834 ± 1313 | 0.5 (0.5-0.9) | 0.5 (0.4-1.0) |
| | | 600 (6) | 4211 ± 2302 | 3604 ± 1742 | 0.5 (0.5-0.5) | 0.5 (0.5-1.0) |
| | D | 600 (6) | 3971 ± 1943 | 4144 ± 2280 | 0.5 (0.5-0.5) | 0.5 (0.5-1.0) |
| | E | 600 (6) | 3412 ± 2175 | 3192 ± 2085 | 0.5 (0.5-1.0) | 0.5 (0.5-1.0) |

TABLE 4A-continued $C_{max}$ and $T_{max}$ for Compound 1 and Metabolite 1-7 at Day 1 and Steady State (SS)

| Analyte | Part | Dose (n) (mg/d) | $C_{max}$ (ng/mL) Day 1 | SS | $T_{max}$ (h) Day 1 | SS |
|---|---|---|---|---|---|---|
| Metabolite 1-7 | C | 150 (6) | 75.6 ± 15.4 | 81.1 ± 33.9 | 4.0 (4.0-6.0) | 4.0 (4.0-8.0) |
|  |  | 300 (6) | 123 ± 16.6 | 220 ± 203 | 4.0 (2.9-6.0) | 4.0 (2.0-5.9) |
|  |  | 600 (6) | 197 ± 57.1 | 233 ± 42.9 | 5.0 (4.0-6.0) | 4.0 (4.0-6.0) |
|  | D | 600 (6) | 195 ± 42.9 | 263 ± 104 | 5.0 (3.0-6.0) | 4.0 (4.0-6.0) |
|  | E | 600 (6) | 201 ± 68.1 | 255 ± 95.4 | 5.0 (3.0-6.0) | 6.0 (4.0-6.0) |

TABLE 4B

AUC and $T_{1/2}$ for Compound 1 and Metabolite 1-7 at Day 1 and Steady State (SS)

| Analyte | Part | Dose (n) (mg/d) | AUC[#] (ng/mL×h) Day 1 | SS | $T_{1/2}$ (h) Day 1 | SS |
|---|---|---|---|---|---|---|
| Compd 1 | C | 150 (6) | 492 ± 141 | 475 ± 301 | 0.62 ± 0.11 | 0.64 ± 0.20 |
|  |  | 300 (6) | 1947 ± 1120 | 1510 ± 976 | 0.80 ± 0.18 | 0.73 ± 0.15 |
|  |  | 600 (6) | 3335 ± 1502 | 4036 ± 2093 | 0.86 ± 0.11 | 0.85 ± 0.12 |
|  | D | 600 (6) | 3333 ± 1241 | 3754 ± 2275 | 0.73 ± 0.12 | 0.83 ± 0.06 |
|  | E | 600 (6) | 3323 ± 1467 | 3527 ± 1605 | 0.86 ± 0.18 | 0.81 ± 0.12 |
| Metabolite 1-7 | C | 150 (6) | 800 ± 213 | 962 ± 409 |  | 12.5 ± 6.33 |
|  |  | 300 (6) | 1414 ± 220 | 1828 ± 453 |  | 24.5 ± 15.3 |
|  |  | 600 (6) | 2204 ± 486 | 2839 ± 572 |  | 28.9 ± 14.4 |
|  | D | 600 (6) | 2253 ± 595 | 3117 ± 1048 |  | 27.9 ± 18.3 |
|  | E | 600 (6) | 2625 ± 873 | 3569 ± 1214 |  | 24.4 ± 9.81 |

[#]$AUC_{inf}$ for Compound 1 and $AUC_\tau$ for Metabolite 1-7

TABLE 4C $C_{24\,h}$ for Compound 1 and Metabolite 1-7 at Day 1 and Steady State (SS)

| Analyte | Part | Dose (n) (mg/d) | $C_{24\,h}$* (ng/mL) Day 1 | SS* |
|---|---|---|---|---|
| Compd 1 | C | 150 (6) |  |  |
|  |  | 300 (6) |  |  |
|  |  | 600 (6) |  |  |
|  | D | 600 (6) |  |  |
|  | E | 600 (6) |  |  |
| Metabolite 1-7 | C | 150 (6) | 8.08 ± 3.48 | 12.8 ± 4.45 |
|  |  | 300 (6) | 18.0 ± 8.83 | 26.1 ± 7.56 |
|  |  | 600 (6) | 27.5 ± 5.21 | 46.9 ± 15.5 |
|  | D | 600 (6) | 30.1 ± 10.9 | 37.8 ± 11.4 |
|  | E | 600 (6) | 41.6 ± 12.9 | 69.9 ± 18.5 |

*$C_{24}$ only reported for Metabolite 1-7; $C_{24}$ at steady state was the mean of $C_{24}$ at 72, 96, 120, 144 and 168 h.

Figure 6A:
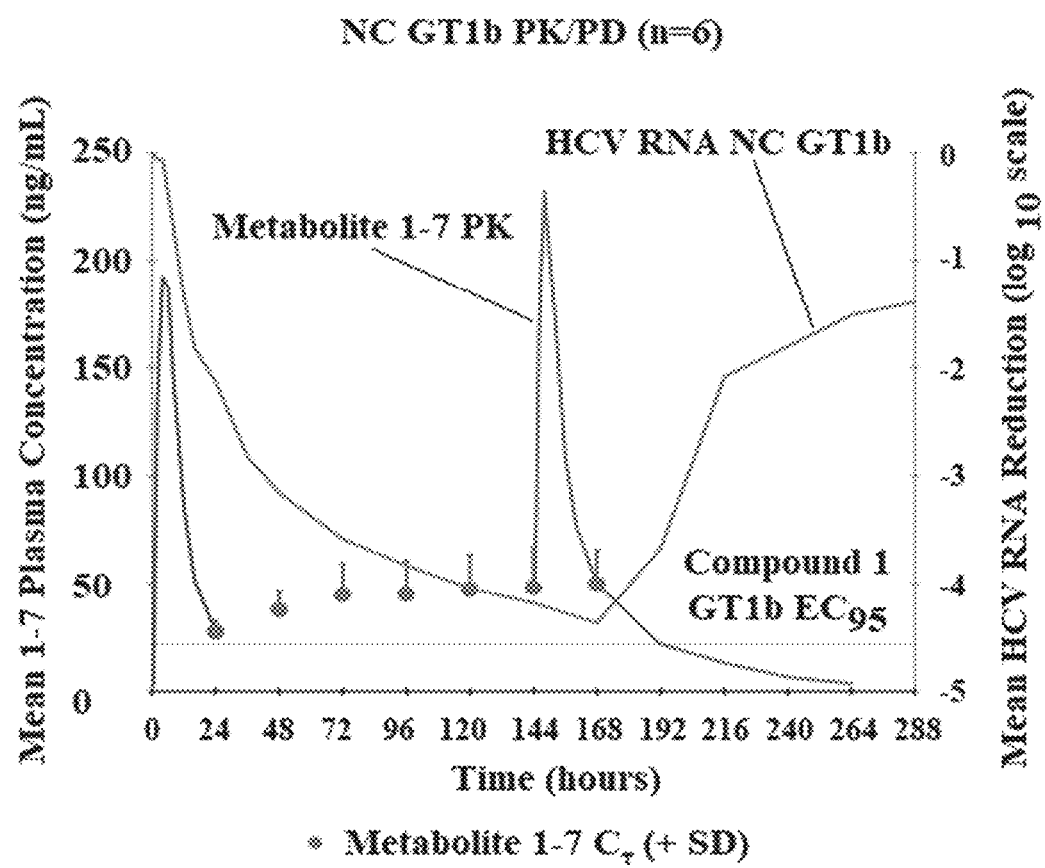
FIG. 6A is a graph plotting the mean metabolite 1-7 plasma concentration (left y-axis) and the mean HCV RNA reduction following 600 mg/day QD of Compound 2 (equivalent to 550 mg of Compound 1) (right y-axis) against time for subjects with non-cirrhotic GT1b HCV infection as described in Examples 3 and 4. The $EC_{95}$ of Compound 1 in GT1b is shown as a horizontal dashed line (- - - - -) The dots represent the steady state plasma trough levels ($C_\tau$) of metabolite 1-7 and as shown in the figure, ($C_\tau$) is consistently above the $EC_{95}$ at all time points studied. The left y-axis is mean metabolite 1-7 plasma concentration measured in ng/mL, the right y-axis is HCV RNA reduction following 550 mg of Compound 1 QD measured in log 10 IU/mL, and the x-axis is time measured in hours.
Figure 6B:
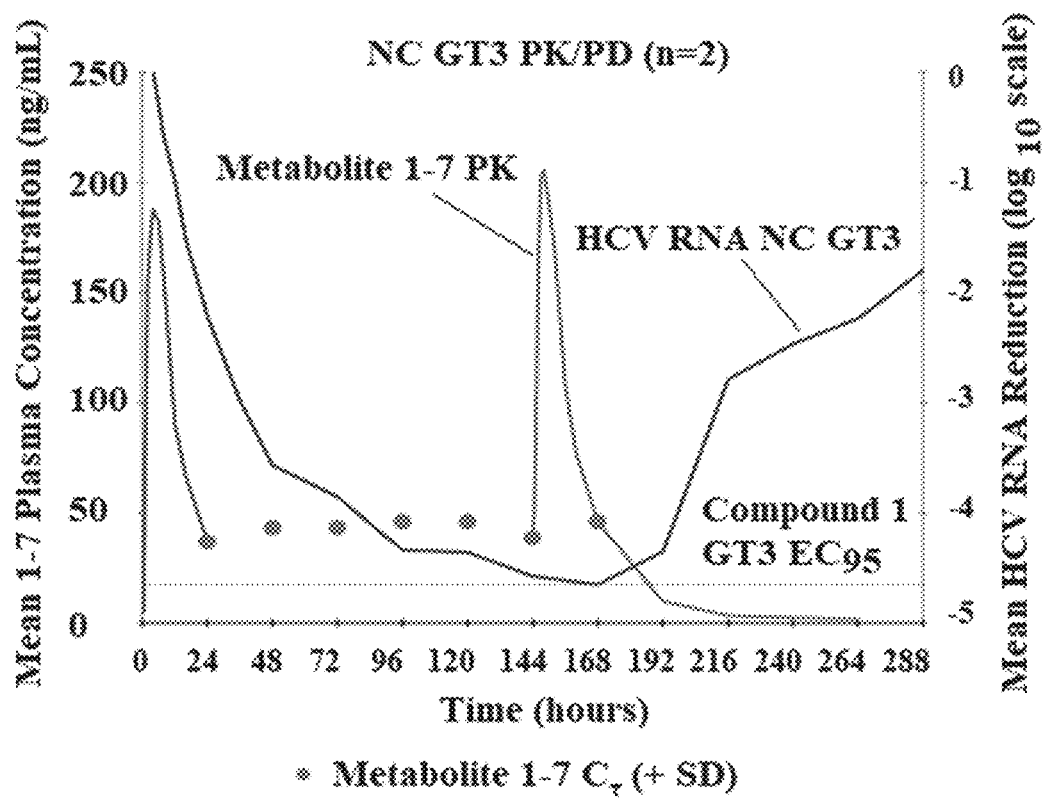
FIG. 6B is a graph plotting the mean metabolite 1-7 plasma concentration (left y-axis) and the mean HCV RNA reduction following 600 mg/day QD of Compound 2 (equivalent to 550 mg of Compound 1) (right y-axis) against time for subjects with non-cirrhotic GT3 HCV infection as described in examples 3 and 4. The $EC_{95}$ of Compound 1 in GT3 is shown as a horizontal dashed line (- - - - -) The dots represent the steady state plasma trough levels ($C_\tau$) of metabolite 1-7 and as shown in the figure, ($C_\tau$) is consistently above the $EC_{95}$ at all time points studied. The left y-axis is mean metabolite 1-7 plasma concentration measured in ng/mL, the right y-axis is HCV RNA reduction following 550 mg of Compound 1 QD measured in log 10 IU/mL, and the x-axis is time measured in hours.
Figure 6C:
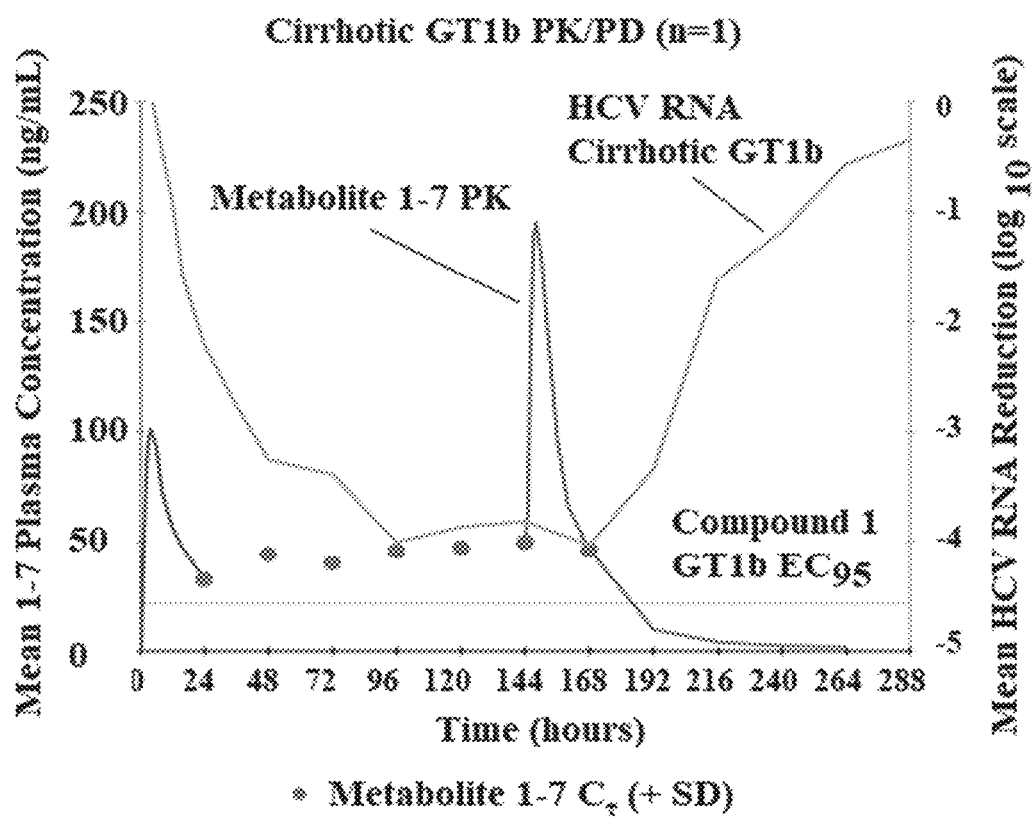
FIG. 6C is a graph plotting the mean metabolite 1-7 plasma concentration (left y-axis) and the mean HCV RNA reduction following 600 mg/day QD of Compound 2 (equivalent to 550 mg of Compound 1) (right y-axis) against time for subjects with cirrhotic GT1b HCV infection as described in Examples 3 and 4. The $EC_{95}$ of Compound 1 in GT1b is shown as a horizontal dashed line (- - - - -) The dots represent the steady state plasma trough levels ($C_\tau$) of metabolite 1-7 and as shown in the figure, ($C_\tau$) is consistently above the $EC_{95}$ at all time points studied. The left y-axis is mean metabolite 1-7 plasma concentration measured in ng/mL, the right y-axis is HCV RNA reduction following 550 mg of Compound 1 QD measured in log 10 IU/mL, and the x-axis is time measured in hours.
Figure 6D:
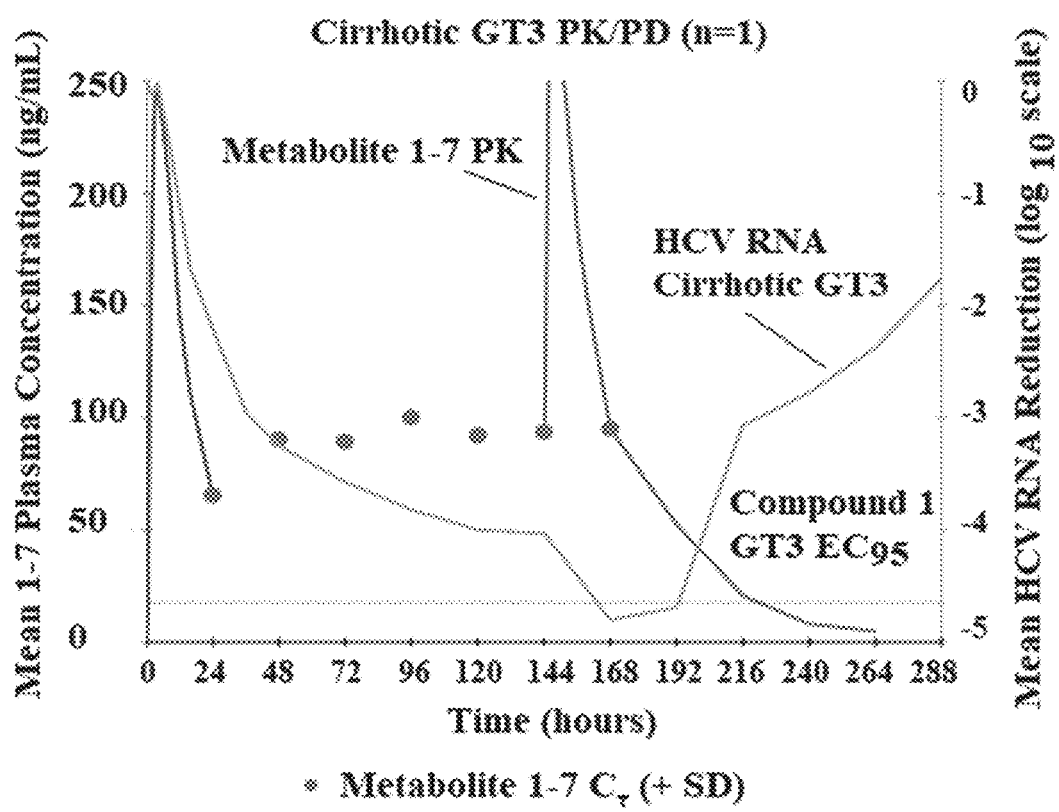
FIG. 6D is a graph plotting the mean metabolite 1-7 plasma concentration (left y-axis) and the mean HCV RNA reduction following 600 mg/day QD of Compound 2 (equivalent to 550 mg of Compound 1) QD (right y-axis) against time for subjects with cirrhotic GT3 HCV infection as described in Examples 3 and 4. The $EC_{95}$ of Compound 1 in GT1b is shown as a horizontal dashed line (- - - - -) The dots represent the steady state plasma trough levels ($C_\tau$) of metabolite 1-7 and as shown in the figure, ($C_\tau$) is consistently above the $EC_{95}$ at all time points studied. The left y-axis is mean metabolite 1-7 plasma concentration measured in ng/mL, the right y-axis is HCV RNA reduction following 550 mg of Compound 1 QD measured in log 10 IU/mL, and the x-axis is time measured in hours.

FIGS. 6A-6D are PK/PD analysis of non-cirrhotic subjects with GT1 HCV infection (FIG. 6A), non-cirrhotic subjects with GT3 HCV infection (FIG. 6B), the cirrhotic subject with GT1 HCV infection (FIG. 6C), and the cirrhotic subject with GT3 HCV infection (FIG. 6D). The left y-axis is the mean metabolite 1-7 concentration and the right y-axis is the mean HCV RNA reduction. The dashed horizontal line (- - - - -) represents the $EC_{95}$ value of Compound 1 and the dots represent $C_\tau$, the steady-state plasma trough level of metabolite 1-7 following 600 mg of Compound 2 (equivalent to 550 mg of Compound 1). As shown in FIGS. 6A-6D and Table 6, the steady state plasma trough level of metabolite 1-7 consistently exceeds the $EC_{95}$ of Compound 1 in inhibiting HCV GT1 and GT3 in non-cirrhotic and cirrhotic subjects. The steady state plasma trough level of metabolite 1-7 in cirrhotic patients is 45.7 ng/mL, and the $EC_{95}$ of Compound 1 in HCV GT1, GT2, and GT3 is approximately 21.7 ng/mL, 11.6 ng/mL, and 17.5 ng/mL equivalents of metabolite 1-7, respectively. FIGS. 6A-6D also demonstrate that antiviral activity correlated with plasma exposure.

Figure 7:
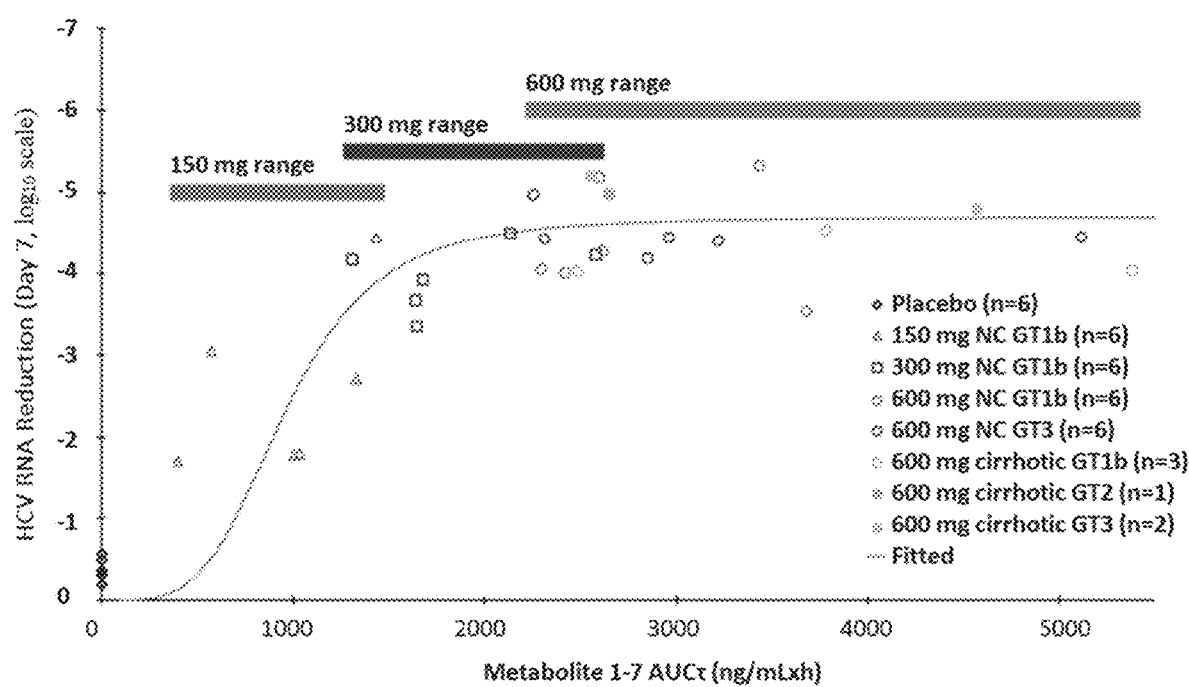
FIG. 7 is an Emax model where the HCV RNA reduction as measured on day 7 for subjects with non-cirrhotic GT1b HCV infection, non-cirrhotic GT3 HCV infection, cirrhotic GT1b HCV, cirrhotic GT2, and cirrhotic GT3 HCV infection is plotted against the AUC of metabolite 1-7 following QD dosing of Compound 2. As described in Examples 3 and 4, subjects with non-cirrhotic GT1b HCV were administered multiple ascending doses of 150 mg, 300 mg, or 600 mg of Compound 2 for 7 days. Subjects with non-cirrhotic GT3 and those with cirrhotic GT1/GT2/GT3 infections were given 600 mg of Compound 2 (equivalent to 550 mg/d of Compound 1) QD for 7 days. The model predicts that metabolite 1-7 exposure of greater than or equal to 2000 ng/mL×h will result in a maximum viral load reduction of at least 4 log after 7 days of dosing. The range for the 150 mg dose was 397-1434 ng/mL×h. The range for the 300 mg dose was 1305-2580 ng/mL×h. The range for the 600 mg dose was 2254-5379 ng/mL×h. All subjects were able to achieve a metabolite 1-7 exposure greater than 2000 ng/mL×h following doses of 600 mg of Compound 2 regardless of whether the subject exhibited cirrhosis or non-cirrhosis of the liver. The x-axis is the AUC of metabolite 1-7 measured in ng/mL×h and the y-axis is the HCV RNA reduction on day 7 measured on a $log_{10}$ scale.

An $E_{max}$ model, generated by plotting the AUC of metabolite 1-7 against the HCV RNA reduction, was used to predict that metabolite 1-7 exposures of ≥2000 ng/mL×h will result in a maximal viral load reduction of at least 4 log units after 7 days of QD dosing with Compound 2 (FIG. 7). As shown in Table 6 and FIG. 7, a 600 mg dose of Compound 2 (equivalent to 550 mg of Compound 1) consistently reaches this threshold in non-cirrhotic and cirrhotic subjects, demonstrating that 550 mg QD of Compound 1 (equivalent to 600 mg of Compound 2) will result in maximum viral-load reduction.

Figure 8A:
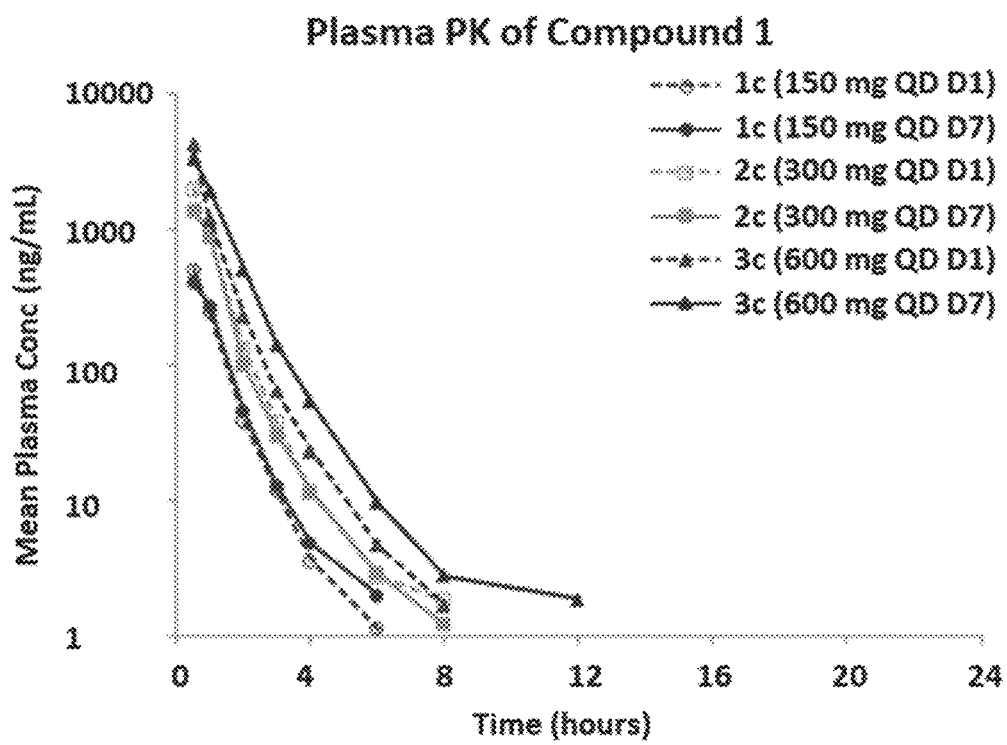
FIG. 8A is graph of the mean plasma concentration of Compound 1 at day 1 (dashed line) and day 7 (solid line) following 150 mg once a day (QD), 300 mg QD, and 600 mg QD of Compound 2. Each solid and dashed line represents a cohort of GT1b non-cirrhotic subjects in Part C of the study as described in Example 4. The x-axis is time measured in hours and the y-axis is mean plasma concentration of Compound 1 measured in ng/mL.
Figure 8B:
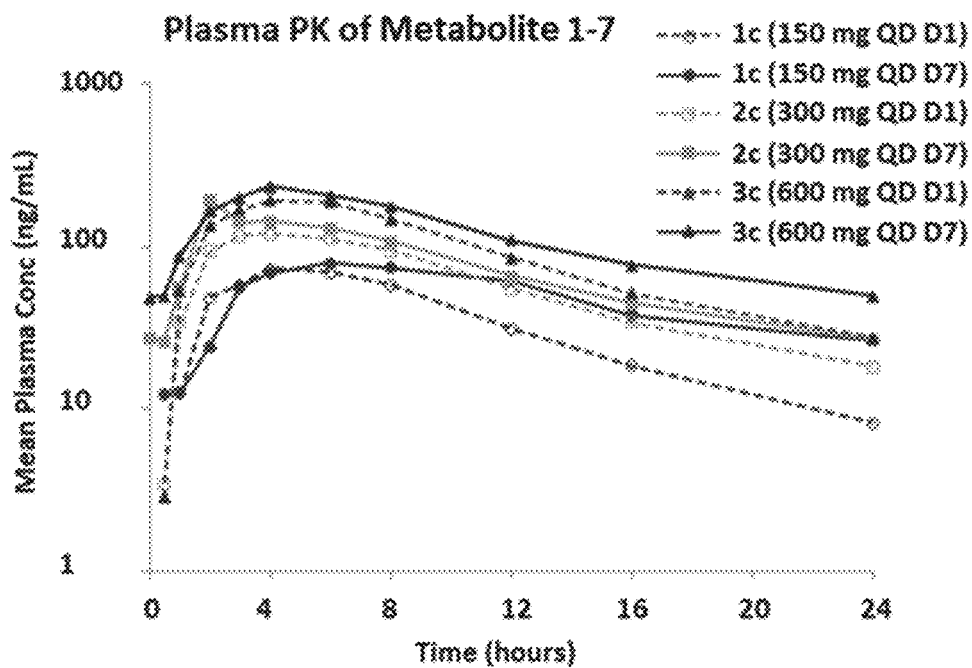
FIG. 8B is graph of the mean plasma concentration of metabolite 1-7 at day 1 (dashed line) and day 7 (solid line) following 150 mg once a day (QD), 300 mg QD, and 600 mg QD of Compound 2. Each solid and dashed line represents a cohort of GT1b non-cirrhotic subjects in Part C of the study as described in Example 4. The x-axis is time measured in hours and the y-axis is mean plasma concentration of metabolite 1-7 measured in ng/mL.
Figure 9A:
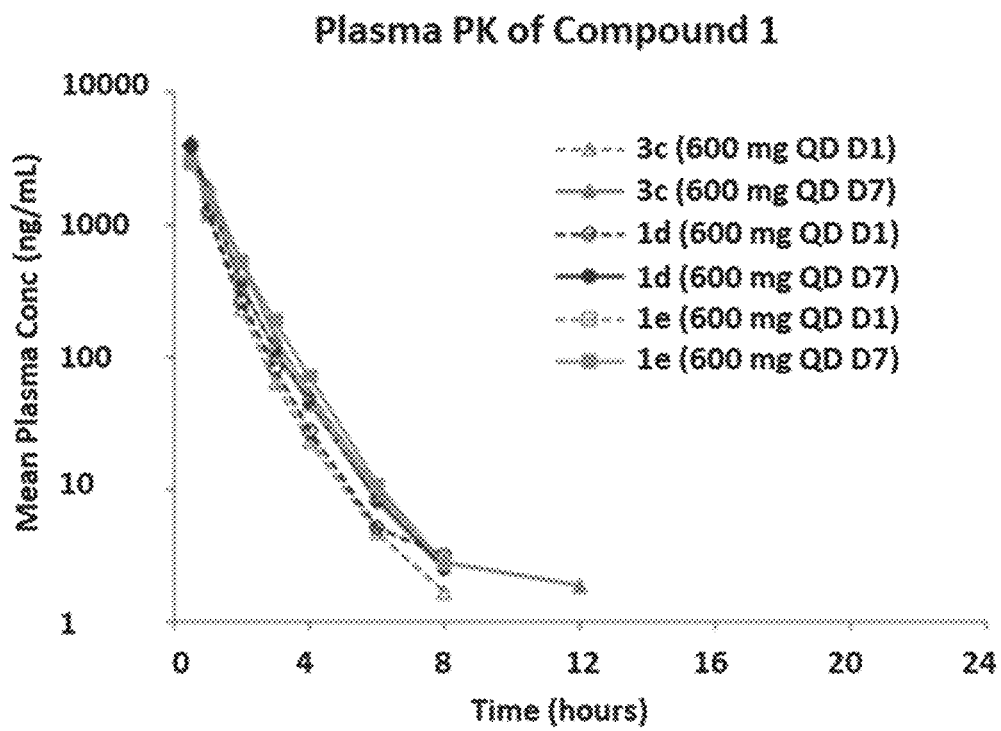
FIG. 9A is graph of the mean plasma concentration of Compound 1 at day 1 (dashed line) and day 7 (solid line) following 600 mg once daily of Compound 2 in GT1b non-cirrhotic (cohorts 3c), GT3 non-cirrhotic (cohorts 1d), and cirrhotic (cohorts 1e) patients as described in Example 4. The x-axis is time measured in hours and the y-axis is mean plasma concentration of Compound 1 measured in ng/mL.
Figure 9B:
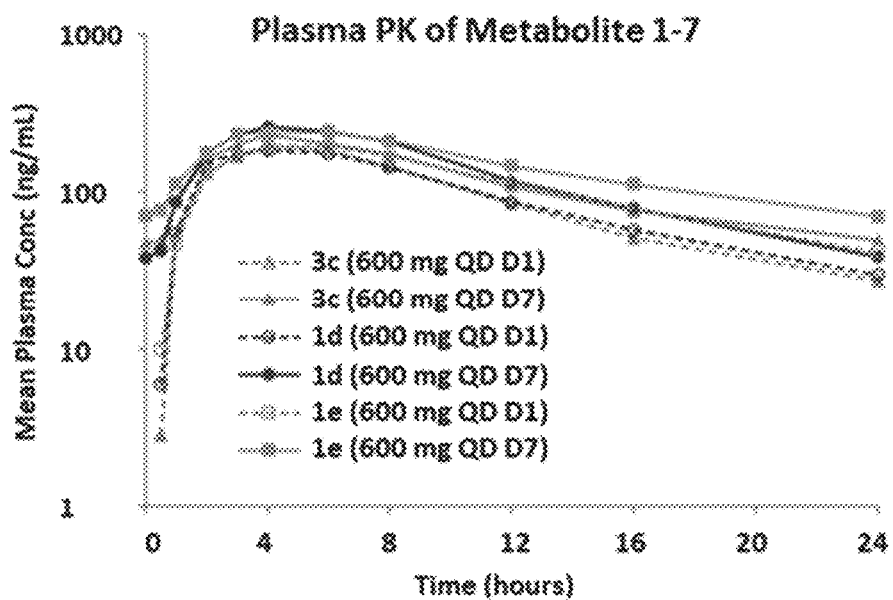
FIG. 9B is graph of the mean plasma concentration of metabolite 1-7 at day 1 (dashed line) and day 7 (solid line) following 600 mg once daily of Compound 2 in GT1b non-cirrhotic (cohorts 3c), GT3 non-cirrhotic (cohorts 1d), and cirrhotic (cohorts 1e) patients as described in Example 4. The x-axis is time measured in hours and the y-axis is mean plasma concentration of metabolite 1-7 measured in ng/mL.
Figure 10:
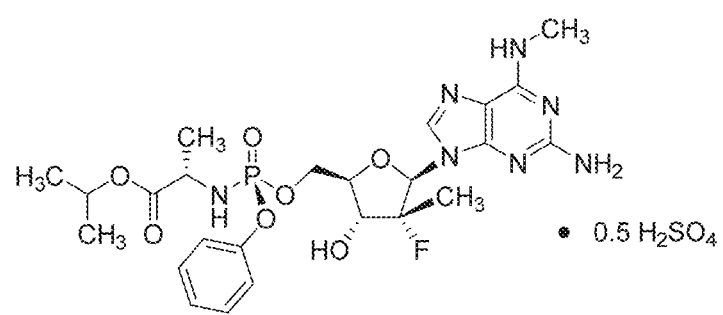
FIG. 10 is the structure of hemi-sulfate salt Compound 2.

Mean plasma concentration-time profiles for ascending Compound 2 doses in subjects without cirrhosis enrolled in Part C of the study are shown in FIG. 8A and FIG. 8B. FIG. 8A is the mean plasma concentration-time profile of Compound 1 following administration of Compound 2. FIG. 8B is the mean plasma concentration-time profile of metabolite 1-7 following administration of 600 mg of Compound 2. FIG. 9A and FIG. 9B are a comparison of plasma concentration-time profiles in patients with and without cirrhosis (FIG. 9A is the profile of Compound 1 and FIG. 9B is the profile of metabolite 1-7). As depicted in FIG. 9B and Table 6, the PK of Compound 1 and metabolite 1-7 were comparable after 600 mg QD of Compound 2, regardless of HCV genotype infection (Part C vs. Part D) or cirrhosis status (Parts C/D vs. Part E). Steady state was reached after the fifth dose in the cohort of subjects with cirrhosis.

Based on the known metabolism of Compound 2, metabolite 1-7 is regarded as the most important metabolite in circulation as it reflects liver conversion of Compound 2 to the active metabolite 1-7. Therefore metabolite 1-7 plasma levels may be a correlate of Compound 2 dose-associated antiviral activity in subjects' livers. For rapidly-replicating viruses such as HCV, maintenance of antiviral activity throughout inter-dose time intervals optimizes efficacy by reducing chances for recrudescent viral replication during inter-dose trough periods. Compound 2 exhibited early and potent viral suppression which correlated well with the plasma PK of metabolite 1-7 regardless of genotype or mild hepatic impairment. After the first 600 mg dose, mean metabolite 1-7 trough concentration (27.5 ng/mL in NC GT1b infected subjects; 30.1 ng/mL in NC GT3 infected subjects; 41.6 ng/mL in subjects with cirrhosis) already exceeded the $EC_{95}$ of Compound 1 in inhibiting replicons containing HCV constructs of clinical isolates (GT1b $EC_{95}$ of ~22 ng/mL metabolite 1-7 equivalent; GT2 $EC_{95}$ of ~12 ng/mL; GT3 $EC_{95}$ of ~18 ng/mL), resulting in very rapid plasma HCV RNA decreases of up to 2.4 $\log_{10}$ IU/mL within the first 24 h of dosing. Upon reaching steady state, metabolite 1-7 troughs were 2- to 6-fold the $EC_{95}$ values (depending on genotype), exerting sustained suppressive pressure on viral replication, leading to ~4.5 $\log_{10}$ IU/mL reductions in plasma HCV RNA regardless of genotype or cirrhosis status. In those cohorts receiving 600 mg QD, ~30% of subjects achieved HCV RNA below the lower limit of quantitation with only seven days of therapy. Further modeling demonstrated that $E_{max}$ was achieved with metabolite 1-7 AUCτ greater than 2000 ng/mL×h and only the 600 mg QD dose produced exposure values that were consistently above this threshold. Overall, Compound 2 monotherapy exhibited very rapid and equally potent antiviral activity regardless of genotype or cirrhosis status. Compound 2 at the highest doses evaluated for seven days was well tolerated in HCV-infected subjects. Compound 2 demonstrated rapid, potent, dose/exposure-related and pan-genotypic antiviral activity with similar responses in those subjects with and without cirrhosis.

This specification has been described with reference to embodiments of the invention. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

What is claimed is:

1. A method to treat a hepatitis C-infected human with decompensated cirrhosis comprising providing an effective amount of a compound of the formula

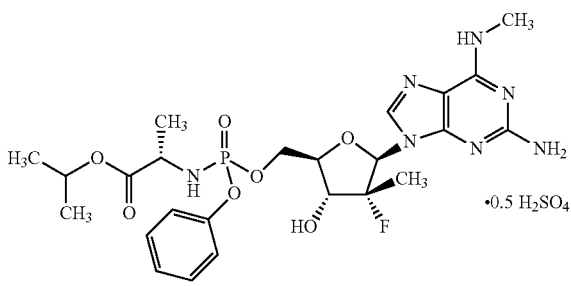 [SMILES: CNc1nc(N)nc2c1ncn2[C@@H]1O[C@H](COP(=O)(N[C@@H](C)C(=O)OC(C)C)Oc2ccccc2)[C@@H](O)[C@@]1(C)F]

optionally in a pharmaceutically acceptable carrier.

2. The method of claim 1, wherein the compound is administered orally.

3. The method of claim 1, wherein the compound is administered parentally.

4. The method of claim 1, wherein the compound is administered intravenously.

5. The method of claim 1, wherein the compound is administered via controlled release.

6. The method of claim 1, wherein at least 400 mg of the compound is administered.

7. The method of claim 1, wherein at least 500 mg of the compound is administered.

8. The method of claim 1, wherein at least 600 mg of the compound is administered.

9. The method of claim 1, wherein at least 700 mg of the compound is administered.

10. The method of claim 1, wherein the compound is administered for up to 12 weeks, for up to 8 weeks, or for up to 6 weeks.

11. The method of claim 1, wherein the compound is administered once a day.

12. The method of claim 1, wherein the compound is administered twice a day.

13. The method of claim 1, wherein the hepatitis C virus is Genotype 1a, 1b, 2a, 2b, 3a, 3b, 4a, 4d, 5a, or 6.

14. The method of claim 13, wherein the hepatitis C virus is Genotype 1a.

15. The method of claim 13, wherein the hepatitis C virus is Genotype 1b.

16. The method of claim 13, wherein the hepatitis C virus is Genotype 2a or 2b.

17. The method of claim 13, wherein the hepatitis C virus is Genotype 3a or 3b.

18. The method of claim 13, wherein the hepatitis C virus is Genotype 4a or 4d.

19. The method of claim 13, wherein the hepatitis C virus is Genotype 5a.

20. The method of claim 1, wherein the compound is of the formula:

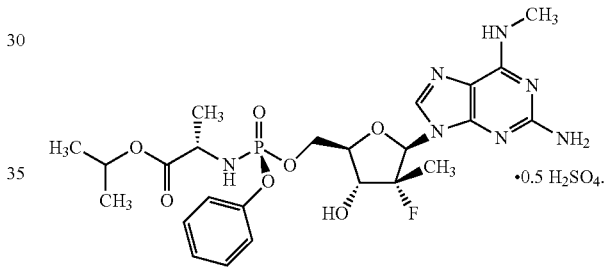

21. The method of claim 20, wherein the compound is administered orally.

22. The method of claim 20, wherein the compound is administered parentally.

23. The method of claim 20, wherein the compound is administered intravenously.

24. The method of claim 20, wherein the compound is administered via controlled release.

25. The method of claim 20, wherein at least 400 mg of the compound is administered.

26. The method of claim 20, wherein at least 500 mg of the compound is administered.

27. The method of claim 20, wherein at least 600 mg of the compound is administered.

28. The method of claim 20, wherein the compound is administered for up to 12 weeks, for up to 8 weeks, or for up to 6 weeks.

29. The method of claim 20, wherein the compound is administered once a day.

30. The method of claim 20, wherein the compound is administered twice a day.

31. The method of claim 20, wherein the hepatitis C virus is Genotype 1a, 1b, 2a, 2b, 3a, 3b, 4a, 4d, 5a, or 6.

32. The method of claim 31, wherein the hepatitis C virus is Genotype 1a.

33. The method of claim 31, wherein the hepatitis C virus is Genotype 1b.

34. The method of claim 31, wherein the hepatitis C virus is Genotype 2a or 2b.

35. The method of claim 31, wherein the hepatitis C virus is Genotype 3a or 3b.

36. The method of claim 31, wherein the hepatitis C virus is Genotype 4a or 4d.

37. The method of claim 31, wherein the hepatitis C virus is Genotype 5a.

\* \* \* \* \*